United States Patent
Mitchell et al.

(10) Patent No.: US 9,162,987 B2
(45) Date of Patent: Oct. 20, 2015

(54) IODO PYRIMIDINE DERIVATIVES USEFUL FOR THE TREATMENT OF MACROPHAGE MIGRATION INHIBITORY FACTOR (MIF)-IMPLICATED DISEASES AND CONDITIONS

(75) Inventors: Robert A. Mitchell, Louisville, KY (US); John O. Trent, Louisville, KY (US); Pooran Chand, Birmingham, AL (US); Gilles Hugues Tapolsky, Louisville, KY (US)

(73) Assignees: University of Louisville Research Foundation, Inc., Louisville, KY (US); Advanced Cancer Therapeutics, LLC, Louisville, KY (US)

( * ) Notice: Subject to any disclaimer, the term of this patent is extended or adjusted under 35 U.S.C. 154(b) by 0 days.

(21) Appl. No.: 13/498,036

(22) PCT Filed: Sep. 24, 2010

(86) PCT No.: PCT/US2010/050206
§ 371 (c)(1),
(2), (4) Date: Dec. 12, 2012

(87) PCT Pub. No.: WO2011/038234
PCT Pub. Date: Mar. 31, 2011

(65) Prior Publication Data
US 2013/0079361 A1    Mar. 28, 2013

Related U.S. Application Data

(60) Provisional application No. 61/245,481, filed on Sep. 24, 2009.

(51) Int. Cl.
| | |
|---|---|
| *C07D 239/02* | (2006.01) |
| *A01N 43/54* | (2006.01) |
| *A61K 31/505* | (2006.01) |
| *C07D 239/30* | (2006.01) |
| *C07D 239/38* | (2006.01) |
| *C07D 239/42* | (2006.01) |
| *C07D 401/04* | (2006.01) |
| *C07D 405/04* | (2006.01) |
| *C07D 409/04* | (2006.01) |

(52) U.S. Cl.
CPC ............ *C07D 239/30* (2013.01); *C07D 239/38* (2013.01); *C07D 239/42* (2013.01); *C07D 401/04* (2013.01); *C07D 405/04* (2013.01); *C07D 409/04* (2013.01)

(58) Field of Classification Search
None
See application file for complete search history.

(56) References Cited

U.S. PATENT DOCUMENTS

| | | | |
|---|---|---|---|
| 7,517,523 | B2 | 4/2009 | Bucala et al. |
| 7,863,313 | B2 | 1/2011 | Morand et al. |
| 8,293,891 | B2 | 10/2012 | Dorsch et al. |
| 2003/0187007 | A1 | 10/2003 | Cao et al. |
| 2005/0130954 | A1* | 6/2005 | Mitchell et al. .......... 514/210.21 |
| 2005/0196795 | A1 | 9/2005 | Siegler et al. |
| 2007/0281924 | A1 | 12/2007 | Gaeta |
| 2008/0317759 | A1 | 12/2008 | Bucala et al. |
| 2011/0009412 | A1 | 1/2011 | Mitchell et al. |
| 2013/0177552 | A1 | 7/2013 | Tezel et al. |

FOREIGN PATENT DOCUMENTS

| | | |
|---|---|---|
| EP | 0 767 170 | 4/1997 |
| WO | WO01/07436 | 2/2001 |
| WO | WO 02/079197 | 10/2002 |
| WO | WO 2005/016914 | 2/2005 |
| WO | WO 2005/121106 | 12/2005 |
| WO | WO2006/005914 | 1/2006 |
| WO | WO 2007140263 A2 * | 12/2007 |
| WO | WO 2008/099000 | 8/2008 |

OTHER PUBLICATIONS

CAS Registration No. 39189-98-5 (Entered Nov. 16, 1984).*
STN CAS RN: 1049024-02-3 (entered Sep. 12, 2008).*
Extended European Search Report corresponding to European Patent Application No. 07811937.7 dated Jun. 17, 2013.
Official Action corresponding to U.S. Appl. No. 12/301,783 dated Aug. 26, 2013.
Official Action corresponding to U.S. Appl. No. 12/301,783 dated Apr. 1, 2014.
Al Abed et al. (2005). ISO-1 binding to the tautomerase active site of MIF inhibits its pro-inflammatory activity and increases survival in severe sepsis. J Biol Chem. 280:36541-36544.

(Continued)

*Primary Examiner* — Craig Ricci
*Assistant Examiner* — Jared D Barsky
(74) *Attorney, Agent, or Firm* — Jenkins, Wilson, Taylor & Hunt, P.A.

(57) ABSTRACT

Compounds useful for the inhibition of macrophage migration inhibitory factor (MIF) are provided herein, having the Formula (I): wherein A is selected from the group consisting of aromatic or non-aromatic rings, bicyclic rings, polycyclic rings, alkenes or alkynes; B is H, OH, OR, SR, NH2, NHR, or alkyl; R is H or alkyl, and X and Y are independently N or CH, but one of X and Y must be N. Also provided are pharmaceutical compositions comprising a Formula I compound and methods for the treatment of MIF-implicated diseases or conditions, comprising administering a safe and effective amount of a Formula I compound.

(I)

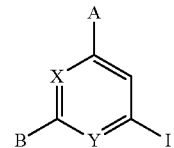

5 Claims, 20 Drawing Sheets

(56) References Cited

OTHER PUBLICATIONS

Altenbach et al., "Structure-Activity Studies on a Series of a 2-Aminopyrimidine-Containing Histamine H4 Receptor Ligands," Journal of Medicinal Chemistry, vol. 51, No. 20, pp. 6571-6580 (Jan. 1, 2008).
Babu et al., Synthesis, Antitumor and Antibacterial Activities of Certain Substituted Pyrimidines Bearing Benzofuran Indian Journal of Pharmaceutical Sciences, vol. 66, No. 5, pp. 647-652 (2004).
Bando et al. (2002). Expression of macrophage migration inhibitory factor in human breast cancer: association with nodal spread. Jpn. J. Cancer Res. 93:389-396.
Brown, J.M. (1993). SR 4233 (tirapazamine): a new anticancer drug exploiting hypoxia in solid tumours. British Journal of Cancer. 67:1163-1170.
Bucala (1996). MIF rediscovered: cytokine, pituitary hormone, and glucocorticoid-induced regulator of the immune response. FASEB J. 14:1607-1613.
Chesney et al. (1999). An essential role for macrophage migration inhibitory factor (MIF) in angiogenesis and the growth of a murine lymphoma. Mol. Med. 5:181-191.
del Vecchio et al. (2000). Macrophage migration inhibitory factor in prostatic adenocarcinoma: correlation with tumor grading and combination endocrine treatment-related changes. Prostate. 45:51-57.
Dios et al. (2002). Inhibition of MIF bioactivity by rational design of pharmacological inhibitors of MIF tautomerase activity: J Med. Chem. 45:2410-2416.
European Search Report corresponding to European Patent Application No. 10819534.8-1452/12480235 dated Apr. 8, 2013.
Fingerle-Rowson et al. (2003). The p53-dependent effects of macrophage migration inhibitory factor revealed by gene targeting. Proc. Natl. Acad.Sci. U.S. A 100: 9354-9359.
Hira et al. (2005). Overexpression of macrophage migration inhibitory factor induces angiogenesis and deteriorates prognosis after radical resection for hepatocellular carcinoma. Cancer. 103:588-598.
International Preliminary Report on Patentability corresponding to International Applicaiton No. PCT/US2007/069672 dated Nov. 28, 2008.
International Search Report corresponding to International Application No. PCT/US2007/069672 dated Aug. 7, 2008.
Kamimura et al. (2000). Intracellular distribution of macrophage migration inhibitory factor predicts the prognosis of patients with adenocarcinoma of the lung. Cancer. 89:334-341.
Koong et al. (2000a). Candidate Genes for the Hypoxic Tumor Phenotype. Cancer Res. 60:883-887.
Koong, et al. (2000b). Pancreatic tumors show high levels of hypoxia Int. J Radiat. Oncol. Bioi Phys. 48:919-922.
Liao et al. (2003). Adhesion-dependent Signaling by Macrophage Migration Inhibitory Factor (MIF). J Bioi Chem. 278:76-81.
Markert et al. (2001). Differential gene expression profiling in human brain tumors. Physiol Genomics. 5, 21-33.
Matsuda et al. (1997). Expression of Macrophage Migration Inhibitory Factor in Corneal Wound Healing in Rats. Invest. Ophthalmol. Vis. Sci. 38:1555-1562.
Matsunaga et al. (1999). Enzyme activity of macrophage migration inhibitory factor toward oxidized catecholamines. J. Biol. Chem. 274:3268-3271.
McInnes et al. (1988). Interleuking 4 induces cultured monocytes/macrophages to form giant multinucleated cells. J. Exp. Med. 167:598-611.
Meyer-Siegler et al. (2002). Macrophage migration inhibitory factor evaluation compared with prostate specific antigen as a biomarker in patients with prostate carcinoma. Cancer. 94:1449-456.
Meyer-Siegler et al. (2005). Further evidence for increased macrophase migration inhibitory factor expression in prostate cancer, BMC Cancer, vol. 5, No. 1, p. 73 (Jul. 6, 2005).
Meyer-Siegler et al. (2006). Inhibition of macrophage migration inhibitory factor or its receptor (CD74) attenuates growth and invasion of DU-145 prostate cancer cells. J Immunol. 177:8730-8739.

Mitchell et al. (1999). Sustained mitogen-activated protein kinase (MAPK) and cytoplasmic phospholipase A2 activation by macrophage migration inhibitory factor (MIF). Regulatory role in cell proliferation and glucocorticoid action. J Bioi Chem. 274:18100-18106.
Mitchell et al. (2002). Macrophage migration inhibitory factor (MIF) sustains macrophage proinflammatory function by inhibiting p53: regulatory role in the innate immune response. Proc. Natl. Acad. Sci. USA. 99:345-350.
Nicoletti et al. (2005). Macrophage migration inhibitory factor (MIF) seems crucially involved in Guillain-Barré syndrome and experimental allergic neuritis. J Neuroimmunol. 168:168-174.
Nimavat et al., Synthesis, anticancer, antitubercular and antimicrobial activity of 1-substituted 3-aryl-5-(3'-bromophenyl)-pyrazolines. Indian Journal of Heterocyclic Chemistry, vol. 12, No. 3, pp. 217-220 (2003).
Notice of Acceptance corresponding to Australian Patent Application No. AU2007267593 dated Mar. 21, 2013.
Notification Concerning Transmittal of International Preliminary Report on Patentability corresponding to International Application No. PCT/US2011/037320 dated Nov. 29, 2012.
Notification of Transmittal of International Search Report and the Written Opinion of the International Searching Authority, or the Declaration corresponding to International Application No. PCT/US10/50206 dated Mar. 29, 2012.
Notification of Transmittal of International Search Report and the Written Opinion of the International Searching Authority, or the Declaration corresponding to International Application No. PCT/US2011/037320 dated Oct. 21, 2011.
Office Action corresponding to Chinese Patent Application 200780028307 dated Nov. 8, 2011.
Office Action corresponding to Japanese Patent Application No. 2009-513395 dated Sep. 7, 2012.
Office Action corresponding to U.S. Appl. No. 12/301,783 dated Dec. 20, 2012.
Office Action corresponding to U.S. Appl. No. 12/301,783 dated Sep. 6, 2012.
Ogawa et al., "An antibody for Macrophase Migration Inhibitory Factor Suppresses Tumour Growth and Inhibits Tumour-Associated Angiogensis," Cytokine, vol. 12, No. 4, pp. 309-314 (2000).
Orita et al. (2001). Coumarin and chromen-4-one analogues as tautomerase inhibitors of macrophage migration inhibitory factor: discovery and X-ray crystallography. J Med. Chem. 44:540-547.
Ouertatani-Sakouhi et al. (2010). Kinetic-based high-throughput screening assay to discover novel classes of macrophase migration inhibitory factor inhibitors. J. Biomol. Screen. 15:347-358.
Petrenko & Moll (2005). Macrophage migration inhibitory factor MIF interferes with the Rb-E2F pathway. Mol. Cell. 17:225-236.
Pozzi et al. (1992). Human recombinant migration inhibitory factor activates human macrophages to kill tumor cells. Cellular Immunol. 145:372-379.
Ren et al. (2005). Macrophage migration inhibitory factor stimulates angiogenic factor expression and correlates with differentiation and lymph node status in patients with esophageal squamous cell carcinoma. Ann. Surg. 242:55-63.
Ren et al. (2006). Inhibition of tumor growth and metastasis in vitro and in vivo by targeting macrophage migration inhibitory factor in human neuroblastoma. Oncogene. 25(25):3501-8.
Rendon et al. (2007). Regulation of human lung adenocarcinoma cell migration and invasion by MIF: Role of Rac1 GTPase and lipid raft assembly. J Biol Chem. 282(41):29910-8.
Senter et al. (2002). Inhibition of macrophage migration inhibitory factor (MIF) tautomerase and biological activities by acetaminophen metabolites. Proc. Natl. Acad. Sci. USA. 99:144-149.
Suzuki et al., "Structure-activity relationships of pyrazine-based CK2 inhibitors: Synthesis and evaluation of 2,6-disubstituted pyrazines and 4,6-disubstituted pyrimidines," Archiv Der Pharmazie, vol. 341, No. 9, pp. 554-561 (Sep. 1, 2008).
Wilson et al. (2005). Macrophage migration inhibitory factor promotes intestinal tumorigenesis. Gastroenterology.129:1485-1503.
Winner et al. (2008). A novel, macrophage migration inhibitory factor suicide substrate inhibits motility and growth of lung cancer cells. 68:7253-7257.

(56) References Cited

OTHER PUBLICATIONS

Wistow et al. (1993). A macrophage migration inhibitory factor is expressed in the differentiating cells of the eye lens. Proc. Natl. Acad. Sci. USA. 90:1272-1275.

Zhong & Bowen (2006). Antiangiogenesis drug design: multiple pathways targeting tumor vasculature. Curr. Med. Chem. 13:849-862.

Notice of Allowance corresponding to U.S. Appl. No. 12/301,783 dated Nov. 28, 2014.

Official Action corresponding to European Patent Application No. 07 811 937.7-1460 dated Mar. 18, 2014.

Official Action corresponding to European Patent Application No. 10 819 534.8-1452 dated Jan. 27, 2015.

Official Action corresponding to European Patent Application No. 10 819 534.8-1452 dated Jun. 20, 2014.

* cited by examiner

MIF Liver Enzyme Inhibition (as a percent of control)

MIF Tumor Enzyme Inhibition (as a percent of control)

Inhibition of cell migration results

A

B

C

D

Tumor growth inhibition of DU145
human prostate xenografts in nude mice

Representative tumor slices for control and treated groups

A

Blood Vessel Density Image
Vehicle Control 5

B

Blood Vessel Density Image
ACT-MIF-002 #4

C

Blood Vessel Density Image
ACT-MIF-001 #7

D

Blood Vessel Density Image
ACT-MIF-003 #8

A  Tumor growth inhibition curves
(average tumor weights; n=5)

B  Survival graph (n=5 initially)

Inhibition of MIF enzyme *in vitro* following dosing of MIF-002

Expression of CD25 in PBMC activated
with Plate bound Anti-CD3 for 48 hours

Red = untreated
Blue = Vehicle (DMSO)
Yellow = 4IPP (25uM)
Green = ACT (25uM)

Expression of CD69 in PBMC activated
with Plate bound Anti-CD3 for 48 hours

Red    = untreated
Blue   = Vehicle (DMSO)
Yellow = 4IPP (25uM)
Green  = ACT (25uM)

IODO PYRIMIDINE DERIVATIVES USEFUL FOR THE TREATMENT OF MACROPHAGE MIGRATION INHIBITORY FACTOR (MIF)-IMPLICATED DISEASES AND CONDITIONS

CROSS-REFERENCE TO RELATED APPLICATIONS

This application is a United States National Stage Application of PCT/US2010/050206, filed Sep. 24, 2010, which itself claimed priority to U.S. Provisional Application Ser. No. 61/245,481, filed Sep. 24, 2009. The disclosure of each of these applications is incorporated herein by reference in its entirety.

The acquisition of migratory and invasive properties by tumor cells is a central and often fatal step in neoplastic disease progression. While normal, non-transformed cells have strict growth factor and adhesive requirements for motility, malignant cells have overcome these requirements through multiple mechanisms including gain of function oncogene mutations, growth factor receptor overexpression and/or constitutive deregulation of extracellular matrix degrading enzymes. Not coincidentally, many solid cancers also possess very low oxygen tensions.

Hypoxia can induce macrophage migration inhibitory factor (MIF) expression. It has been demonstrated that MIF expression is increased in pre-malignant, malignant, and metastatic tumors. Breast, prostate, colon, brain, skin and lung-derived tumors have all been shown to contain significantly higher levels of MIF message and protein than their non-cancerous cell counterparts. MIF expression closely correlates with tumor aggressiveness and metastatic potential, possibly suggesting an important contribution to disease severity by MIF. MIF has been indirectly implicated in tumor growth and progression by stimulating tumor-dependent stromal processes such as neovascularization. Further, MIF has been implicated in macrophage and lymphocyte activation and survival and may play a role in inflammatory disorder progression.

Thus, certain aggressive tumors appear to possess an important functional requirement for MIF in maintaining optimal growth and progression. MIF therefore provides a valuable target for development of therapeutics for the treatment of cancer. Further, MIF may be important in the progression of inflammatory disorders. The need exists to develop therapeutic molecules that target MIF and modulate one or more biological activities of MIF for the treatment of cancers and other inflammatory disorders.

Moreover, MIF is produced by several different pathogens including parasitic helminths, spirochetes and plasmodium. As such, irreversible inhibitors of MIF such as 4-iodo-6-phenylpyrimidine (4-IPP) and analogs may be excellent antagonists of parasite-derived MIF. The need exists to develop therapeutic molecules that target MIF and ameliorate the disease-causing pathologies associated with these and other MIF-producing pathogens.

In one embodiment of the invention, a compound or its enantiomeric or diastereomeric form or a pharmaceutically acceptable salt, prodrug, or metabolite thereof is provided, said compound having the formula:

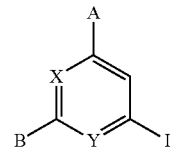

Formula I wherein:
A is selected from the group consisting of: i) substituted or unsubstituted 5, 6 or 7-membered aromatic or nonaromatic rings having 0 or 1 to 4 heteroatoms selected from the group consisting of N, O, S, and combinations thereof; ii) substituted or unsubstituted bicyclic ring; iii) substituted or unsubstituted polycyclic rings; and iv) substituted or unsubstituted alkenes and alkynes having 2 to 10 carbon atoms with 1 to 3 double or triple bonds; B is H, OH, OR, SR, $NH_2$, NHR, alkyl or substituted alkyl or A, but when B is A, A is H or halo; R is H, alkyl or substituted alkyl of 2 to 20 carbon atoms; and X and Y are independently N or CH, but one of X and Y must be N.

In another embodiment, a pharmaceutical composition is provided, comprising: a) an effective amount of a Formula I compound or its enantiomeric or diastereomeric form or a pharmaceutically acceptable salt, prodrug, or metabolite thereof, and b) one or more pharmaceutically acceptable excipients.

In another embodiment, a method for treating a macrophage migration inhibitory factor (MIF)-implicated disease or condition is provided, the method comprising administering to a patient in need thereof an effective amount of a Formula I compound, or its enantiomeric or diastereomeric form or a pharmaceutically acceptable salt, prodrug, or metabolite thereof.

These and other objects, features, embodiments, and advantages will become apparent to those of ordinary skill in the art from a reading of the following detailed description and the appended claims.

Figure 1:
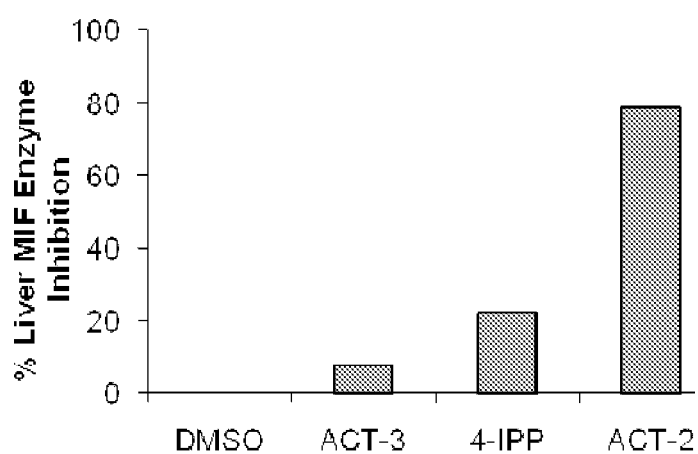
FIG. 1 depicts MIF liver enzyme inhibition as a percent of control, comparing ACT-MIF-003, ACT-MIF-002, and 4-IPP.

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "enantiomer" and "diastereomer" have the standard art recognized meanings (see, e.g., *Hawley's Condensed Chemical Dictionary*, 14th ed.). The illustration of specific protected forms and other derivatives of the compounds of the instant invention is not intended to be limiting. The application of other useful protecting groups, salt forms, etc. is within the ability of the skilled artisan.

The term "prodrug" refers to any covalently bonded carriers which release the active parent drug according to the Formula I described above in vivo when such prodrug is administered to a subject. Prodrugs of the compounds are prepared by modifying functional groups present in the compounds in such a way that the modifications are cleaved, either in routine manipulation or in vivo, to the parent compounds.

The term "substituted" is defined herein as "encompassing moieties or units which can replace one or more hydrogen atoms of a hydrocarbyl moiety. The term "hydrocarbyl" is defined herein as any organic unit or moiety which is comprised of carbon atoms and hydrogen atoms.

"Halo" or "halogen" refers to fluoro, chloro, bromo or iodo.

The term "aromatic ring" refers to an aromatic hydrocarbon ring system. Suitable aromatic rings of embodiments of the present invention contain 5, 6, or 7 carbon atoms in the ring. Aromatic rings can also contain 0 or 1-4 heteroatoms selected from the group consisting of N, O, S, and combinations thereof. Non-limiting examples of suitable aromatic rings include phenyl, pyridinyl, pyrimidinyl, pyridazinyl, furanyl, thiophenyl, pyrrolyl, imidazolyl, pyrazolyl, and thiadiazolyl. Aromatic rings of the present invention can be unsubstituted or substituted with from 1 to 3 substituents. Non-limiting examples of suitable substituents include halo, hydroxyl, alkoxy, amino, substituted amino, carboxylic acid, ester, amide, substituted amide, nitro, alkyl, substituted alkyl, combinations thereof, or functional equivalents thereof.

The term "non-aromatic ring" refers to a non-aromatic saturated or unsaturated hydrocarbon ring system. Suitable non-aromatic rings of embodiments of the present invention contain 5, 6, or 7 carbon atoms in the ring. Non-aromatic rings can also contain 0 or 1-4 heteroatoms selected from the group consisting of N, O, S, and combinations thereof. Non-aromatic rings of the present invention can be unsubstituted or substituted with from 1 to 3 substituents. Non-limiting examples of suitable substituents include halo, hydroxyl, alkoxy, amino, substituted amino, carboxylic acid, ester, amide, substituted amide, nitro, alkyl, substituted alkyl, combinations thereof, or functional equivalents thereof.

The term "bicyclic ring" refers to two fused hydrocarbon rings that may optionally include one or more heteroatoms as ring members. A bicyclic ring can be substituted or unsubstituted, including single or multiple substitutions. The rings can independently show a different degree of saturation and may be saturated, unsaturated, or aromatic. Fusion of the rings can occur in three ways: across a bond between two atoms; across a sequence of atoms (bridgehead); or at a single atom (spirocyclic). Bicyclic rings of the present invention include, but are not limited to, 6-5, 6-6, 6-7, 5-5, 5-6, 5-7, 7-5, and 7-6 ring systems, wherein the integers refer to the number of carbon atoms or heteroatoms in each ring in the structure. Bicylic rings of the present invention can be unsubstituted or substituted with from 1 to 4 substituents. Non-limiting examples of suitable substituents include halo, hydroxyl, alkoxy, amino, substituted amino, carboxylic acid, ester, amide, substituted amide, nitro, alkyl, substituted alkyl, combinations thereof, or functional equivalents thereof. Non-limiting examples of suitable bicyclic rings of the present invention include indole, quinoline and naphthalene.

The term "polycyclic ring" refers to three or more fused hydrocarbon rings that may optionally include one or more heteroatoms as ring members. A polycyclic ring can be substituted or unsubstituted, including single or multiple substitutions. The rings can independently show a different degree of saturation and may be saturated, unsaturated, or aromatic. Fusion of the rings can occur in three ways: across a bond between two atoms; across a sequence of atoms (bridgehead); or at a single atom (spirocyclic). Polycyclic rings of the present invention can be unsubstituted or substituted with from 1 to 4 substituents. Non-limiting examples of suitable substituents include halo, hydroxyl, alkoxy, amino, substituted amino, carboxylic acid, ester, amide, substituted amide, nitro, alkyl, substituted alkyl, combinations thereof, or functional equivalents thereof.

The term "alkene" refers herein to a hydrocarbon chain having from 1 to 3 carbon-carbon double bonds and having 2 to 10 carbon atoms. Alkenes of the present invention can be unsubstituted or substituted with from 1 to 3 substituents. Non-limiting examples of suitable substituents include halo, hydroxyl, alkoxy, amino, substituted amino, carboxylic acid, ester, amide, substituted amide, nitro, alkyl, substituted alkyl, combinations thereof, or functional equivalents thereof.

The term "alkyne" refers herein to a hydrocarbon chain having from 1 to 3 carbon-carbon triple bonds and having 2 to 10 carbon atoms. Alkynes of the present invention can be unsubstituted or substituted with from 1 to 3 substituents. Non-limiting examples of suitable substituents include halo, hydroxyl, alkoxy, amino, substituted amino, carboxylic acid, ester, amide, substituted amide, nitro, alkyl, substituted alkyl, combinations thereof, or functional equivalents thereof.

The term "alkyl" refers to a saturated hydrocarbon chain having 2 to 20 carbon atoms. Alkyls of the present invention can be substituted or unsubstituted. Non-limiting examples of suitable substituents include hydroxyl, amino, thiol, morpholino, pyrrolidino, piperidino, glycol, and polyethyleneglycol (PEG) having molecular weight of 200 to 20,000.

The term "pharmaceutically-acceptable excipient," as used herein, means any physiologically inert, pharmacologically inactive material known to one skilled in the art, which is compatible with the physical and chemical characteristics of the particular CEL inhibitor selected for use. Pharmaceutically-acceptable excipients include, but are not limited to, polymers, resins, plasticizers, fillers, lubricants, diluents, binders, disintegrants, solvents, co-solvents, buffer systems, surfactants, preservatives, sweetening agents, flavoring agents, pharmaceutical grade dyes or pigments, and viscosity agents.

The term "MIF-implicated disease or condition" refers to a disease or condition for which MIF is a factor in the onset and/or progression of the disease or condition.

The term "safe and effective amount" of a Formula (I) compound is an amount that is effective to inhibit the MIF enzyme in an animal, specifically a mammal, more specifically a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the excipient employed, the solubility of the Formula (I) compound therein, and the dosage regimen desired for the composition.

The term "inflammatory disease" refers to a disease characterized by inflammation, or the complex vascular and immune response to harmful stimuli. Inflammatory diseases include those diseases in which inflammation and immune cells are involved in the pathology of the disease. In a specific embodiment, the inflammatory disease is selected from the group consisting of dermatitis, arthritis, rheumatoid arthritis, insulin-dependent diabetes, proliferative vascular disease, acute respiratory distress syndrome, sepsis, septic shock, psoriasis, asthma, cytokine related toxicity, lupus, multiple sclerosis, transplant-host response, and autoimmune disorders.

Compounds according to the present invention have the following generic structure:

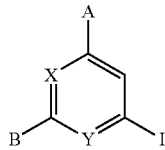

Formula I wherein:
A is selected from the group consisting of:
i) substituted or unsubstituted 5, 6 or 7-membered aromatic or nonaromatic rings having 0 or 1 to 4 heteroatoms selected from the group consisting of N, O, S, and combinations thereof;
ii) substituted or unsubstituted bicyclic ring;
iii) substituted or unsubstituted polycyclic rings; and
iv) substituted or unsubstituted alkenes and alkynes having 2 to 10 carbon atoms with 1 to 3 double or triple bonds;
B is H, OH, OR, SR, $NH_2$, NHR, alkyl or substituted alkyl or A, but when B is A, A is H or halo;
R is H, alkyl or substituted alkyl of 2 to 20 carbon atoms; and
X and Y are independently N or CH, but one of X and Y must be N.

In one embodiment, A is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof; B is H; and X and Y are both N.

In another embodiment, A is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof; B is H, OH, OR, SR, $NH_2$, NHR, alkyl, or substituted alkyl; X and Y are both N.

In another embodiment, A is halo, B is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof, and X and Y are both N.

In another embodiment, A is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof; B is H; X is N, and Y is CH.

In still another embodiment, A is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof; B is H; X is CH; and Y is N.

In another embodiment, A is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof; B is H, OH, OR, SR, $NH_2$, NHR, alkyl or substituted alkyl; X is N and Y is CH.

In still another embodiment, A is selected from the group consisting of: substituted or unsubstituted 5, 6 or 7-membered aromatic or nonaromatic rings having none or 1 to 4 heteroatoms which could be a single atom or the combination of N, O and S; substituted or unsubstituted bicyclic ring, for example indole, quinoline and naphthalene; substituted or unsubstituted polycyclic rings; and substituted or unsubstituted alkenes and alkynes having 2 to 10 carbon atoms with 1 to 3 double or triple bonds; wherein substitutions for any of the above are selected from the group consisting of halo, hydroxyl, alkoxy, amino, substituted amino, carboxylic acid, ester, amide, substituted amide, nitro, alkyl, substituted alkyl, combinations thereof, or functional equivalents thereof; B is H, OH, OR, SR, $NH_2$, NHR, alkyl, or substituted alkyl; X is CH; and Y is N.

In another embodiment, the compound is selected from the group set forth in Table 1.

TABLE 1

| EXAMPLE | ACT-MIF NO. | CHEMICAL NAME |
|---|---|---|
| 2 | ACT-MIF-001 | 4-Iodo-6-(2,3-difluoro-4-methoxyphenyl)pyrimidine |
| 3 | ACT-MIF-002 | 4-Iodo-6-(2-fluoro-4-methoxyphenyl)pyrimidine |
| 4 | ACT-MIF-003 | 4-Iodo-6-(2-fluorophenyl)pyrimidine |
| 5 | ACT-MIF-004 | 4-Iodo-6-(4-fluorophenyl)pyrimidine |
| 6 | ACT-MIF-005 | 4-Iodo-6-(furan-3-yl)pyrimidine |
| 7 | ACT-MIF-006 | 4-Iodo-6-(pyridin-3-yl)pyrimidine |
| 8 | ACT-MIF-008 | 4-Iodo-6-(3-fluorophenyl)pyrimidine |
| 9 | ACT-MIF-010 | 4-Iodo-6-(4-tert-butyloxymethylphenyl)pyrimidine |
| 10 | ACT-MIF-011 | 4-Iodo-6-(2-fluoropyridin-3-yl)pyrimidine |
| 11 | ACT-MIF-012 | 4-Iodo-6-(furan-2-yl)pyrimidine |
| 12 | ACT-MIF-013 | 4-Iodo-6-(4-fluoropyrimidin-3-yl)pyrimidine |
| 13 | ACT-MIF-014 | 4-Iodo-6-(3-fluoro-4-methoxyphenyl)pyrimidine |
| 14 | ACT-MIF-015 | 4-Iodo-6-(2-chloropyridin-5-yl)pyrimidine |
| 15 | ACT-MIF-016 | 4-Iodo-6-(2-hydroxyphenyl)pyrimidine |
| 16 | ACT-MIF-017 | 4-Iodo-6-(2,4-difluorophenyl)pyrimidine |
| 17 | ACT-MIF-018 | 4-Iodo-6-(2-fluoro-6-methoxyphenyl)pyrimidine |
| 18 | ACT-MIF-019 | 4-Iodo-6-(2-chlorophenyl)pyrimidine |
| 19 | ACT-MIF-021 | 4-Iodo-6-(3-acetylaminophenyl)pyrimidine |
| 20 | ACT-MIF-022 | 4-Iodo-6-(thiophen-3-yl)pyrimidine |
| 21 | ACT-MIF-023 | 4-Iodo-6-(3-hydroxymethylphenyl)pyrimidine |
| 22 | ACT-MIF-025 | 4-Iodo-6-(isoquinolin-4-yl)pyrimidine |
| 23 | ACT-MIF-027 | 4-Iodo-6-(2,4,5-trifluorophenyl)pyrimidine |
| 24 | ACT-MIF-028 | 4-Iodo-6-(2,4-difluoropyridin-3-yl)pyrimidine |
| 25 | ACT-MIF-029 | 4-Iodo-6-(4-methoxypyridin-3-yl)pyrimidine |
| 26 | ACT-MIF-030 | 4-Iodo-6-(thiophen-2-yl)pyrimidine |
| 27 | ACT-MIF-032 | 4-Iodo-6-(3,4-difluorophenyl)pyrimidine |
| 28 | ACT-MIF-033 | 4-Iodo-6-(4-ethoxyphenyl)pyrimidine |
| 29 | ACT-MIF-034 | 4-Iodo-6-(4-aminocarbonylphenyl)pyrimidine |
| 30 | ACT-MIF-035 | 4-Iodo-6-(3-aminocarbonylphenyl)pyrimidine |
| 31 | ACT-MIF-036 | 4-Iodo-6-(quinolin-4-yl)pyrimidine |
| 32 | | 4-Iodo-6-(quinolin-8yl)pyrimidine |
| 33 | | 4-Iodo-6-(quinolin-3-yl)pyrimidine |
| 34 | | 4-Iodo-6-(isoquinolin-5-yl)pyrimidine |
| 36 | | 2-Methylthio-4-iodo-6-phenylpyrimidine |
| 37 | | 2-Ethylthio-4-iodo-6-phenylpyrimidine |
| 38 | | 2-Isopropylthio-4-iodo-6-phenylpyrimidine |
| 39 | | 2-n-Butylthio-4-iodo-6-phenylpyrimidine |
| 41 | | 2-Methylamino-4-iodo-6-phenylpyrimidine |
| 42 | | 2-Ethylamino-4-iodo-6-phenylpyrimidine |
| 43 | | 2-Propylamino-4-iodo-6-phenylpyrimidine |
| 44 | | 2-Isopropylamino-4-iodo-6-phenylpyrimidine |
| 45 | | 2-n-Butylamino-4-iodo-6-phenylpyrimidine |
| 46 | | 4-Iodo-6-(benzothiophen-2-yl)pyrimidine |
| 47 | | 4-Iodo-6-(benzofuran-2-yl)pyrimidine |
| 48 | | 4-Iodo-6-(4-hydroxybenzothiophen-2-yl)pyrimidine |
| 49 | | 4-Iodo-6-(4-acetylaminobenzothiophen-2-yl)pyrimidine |
| 50 | | 4-Iodo-6-(4-aminocarbonylbenzothiophen-2-yl)pyrimidine |
| 51 | | 4-Iodo-6-(5-acetylaminopyridin-3-yl)pyrimidine |
| 52 | | 4-Iodo-6-(5-aminocarbonylpyridin-3-yl)pyrimidine |
| 53 | | 4-Iodo-6-(4-fluoropyridin-3-yl)pyrimidine |
| 54 | | 4-Iodo-6-(4-acetylaminothiophen-2-yl)pyrimidine |
| 55 | | 4-Iodo-6-(4-aminocarbonylthiophen-2-yl)pyrimidine |
| 56 | | 4-Iodo-6-(4-methoxythiophen-2-yl)pyrimidine |

In another embodiment, X and Y are both N. In another embodiment, when X and Y are both N, B is H.

In still another embodiment, A is halo, B is A, and X and Y are both N. In a specific embodiment, A is I, B is A, and X and Y are both N.

In another embodiment, X is N and Y is CH. In still another embodiment, when X is N and Y is CH, B is H.

In another embodiment, X is CH and Y is N. In a further embodiment, when X is CH and Y is N, B is H.

In a specific embodiment, A is selected from the group consisting of indole, quinoline, and naphthalene.

In a very specific embodiment, the compound is 4-Iodo-6-(2-fluorophenyl)pyrimidine or 4-Iodo-6-(3-aminocarbonylphenyl)pyrimidine.

In another embodiment, a pharmaceutical composition is provided, comprising:
a) a safe and effective amount of a compound or its enantiomeric or diastereomeric form or a pharmaceutically acceptable salt, prodrug, or metabolite thereof, said compound having the formula:

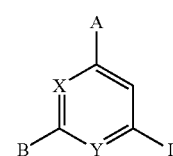

Formula I wherein:
A is selected from the group consisting of:
i) substituted or unsubstituted 5, 6 or 7-membered aromatic or nonaromatic rings having 0 or 1 to 4 heteroatoms selected from the group consisting of N, O, S, and combinations thereof;

ii) substituted or unsubstituted bicyclic ring;

iii) substituted or unsubstituted polycyclic rings; and iv) substituted or unsubstituted alkenes and alkynes having 2 to 10 carbon atoms with 1 to 3 double or triple bonds;

B is H, OH, OR, SR, $NH_2$, NHR, alkyl or substituted alkyl or A, but when B is A, A is H or halo;

R is H, alkyl or substituted alkyl of 2 to 20 carbon atoms; and

X and Y are independently N or CH, but one of X and Y must be N; and b) one or more pharmaceutically acceptable excipients.

In one embodiment, the compound is selected from the group set forth in Table 1.

In another embodiment, X and Y are both N. In another embodiment, when X and Y are both N, B is H.

In still another embodiment, A is halo, B is A, and X and Y are both N. In a specific embodiment, A is I, B is A, and X and Y are both N.

In another embodiment, X is N and Y is CH. In still another embodiment, when X is N and Y is CH, B is H.

In another embodiment, X is CH and Y is N. In a further embodiment, when X is CH and Y is N, B is H.

In a specific embodiment, A is selected from the group consisting of indole, quinoline, and naphthalene.

In a very specific embodiment, the compound is 4-Iodo-6-(2-fluorophenyl)pyrimidine or 4-Iodo-6-(3-aminocarbonylphenyl)pyrimidine.

In a further embodiment, a method for treating a macrophage migration inhibitory factor (MIF)-implicated disease or condition is provided, the method comprising administering to a patient in need thereof a safe and effective amount of a compound or its enantiomeric or diastereomeric form or a pharmaceutically acceptable salt, prodrug, or metabolite thereof, said compound having the formula:

Formula I wherein:

A is selected from the group consisting of:

i) substituted or unsubstituted 5, 6 or 7-membered aromatic or nonaromatic rings having 0 or 1 to 4 heteroatoms selected from the group consisting of N, O, S, and combinations thereof;

ii) substituted or unsubstituted bicyclic ring;

iii) substituted or unsubstituted polycyclic rings; and iv) substituted or unsubstituted alkenes and alkynes having 2 to 10 carbon atoms with 1 to 3 double or triple bonds;

B is H, OH, OR, SR, $NH_2$, NHR, alkyl or substituted alkyl or A, but when B is A, A is H or halo;

R is H, alkyl or substituted alkyl of 2 to 20 carbon atoms; and

X and Y are independently N or CH, but one of X and Y must be N.

In one embodiment, the compound is selected from the group set forth in Table 1.

In another embodiment, X and Y are both N. In another embodiment, when X and Y are both N, B is H.

In still another embodiment, A is halo, B is A, and X and Y are both N. In a specific embodiment, A is I, B is A, and X and Y are both N.

In another embodiment, X is N and Y is CH. In still another embodiment, when X is N and Y is CH, B is H.

In another embodiment, X is CH and Y is N. In a further embodiment, when X is CH and Y is N, B is H.

In a specific embodiment, A is selected from the group consisting of indole, quinoline, and naphthalene.

In a very specific embodiment, the compound is 4-Iodo-6-(2-fluorophenyl)pyrimidine or 4-Iodo-6-(3-aminocarbonylphenyl)pyrimidine.

In one embodiment, the MIF-implicated disease is selected from the group consisting of inflammatory disease and cancer.

In a specific embodiment, the inflammatory disease is selected from the group consisting of dermatitis, arthritis, rheumatoid arthritis, insulin-dependent diabetes, proliferative vascular disease, acute respiratory distress syndrome, sepsis, septic shock, psoriasis, asthma, cytokine related toxicity, lupus, multiple sclerosis, transplant-host response, and autoimmune disorders.

MIF is produced by several different pathogens, including parasitic helminths, spirochetes, and plasmodium. Thus, irreversible inhibitors of MIF, such as the MIF inhibitors of Formula I, are useful as antagonists of parasite-derived MIF. Accordingly, in a further embodiment, the MIF-implicated condition is caused by a MIF-producing pathogen. In a specific embodiment, the MIF-producing pathogen is selected from the group consisting of parasitic helminths, spirochetes, and plasmodium.

EXAMPLES

These following exemplary embodiments and synthetic schemes are provided by way of illustration only and are in no way intended to limit the scope of the present invention.

Example 1

Methods for the preparation of 4-iodo-6-arylpyrimidine derivatives, where aryl is substituted phenyl, heterocyclic or bicyclic ring Scheme 1

General Procedure:

4,6-Dichloropyrimidine (1) is reacted with corresponding aryl boronic acid (2) in dioxane- and aqueous sodium carbonate in the presence of a catalyst used for Suzuki coupling at 50 to 100 C temperature. The resultant 4-chloro-6-arylpyrimidine (3) is isolated by crystallization or column chromatography on silica gel and is converted to corresponding 4-iodo-6-arylpyrimidine (4) using hydroiodic acid. Further treatment of HI may be needed when the reaction is not complete.

The compounds of Examples 2-34 are prepared using Scheme 1.

Example 2

4-Iodo-6-(2,3-difluoro-4-methoxyphenyl)pyrimidine (ACT-MIF-001)

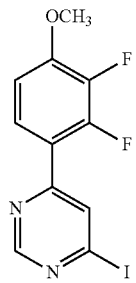 [SMILES: COc1ccc(-c2cc(I)ncn2)c(F)c1F]

The compound was prepared according to Example 1 using 2,3-difluoro-4-methoxyphenylboronic acid and 4,6-dichloropyrimidine. The resultant chloro compound was converted to iodo with hydroiodic acid as described in the general procedure.

$^1$H NMR (DMSO-d$_6$): δ 8.98 (s, 1H), 8.30 (s, 1H), 7.92 (m, 1H), 7.21 (m, 1H), 3.98 (s, 3H).

Example 3

4-Iodo-6-(2-fluoro-4-methoxyphenyl)pyrimidine (ACT-MIF-002)

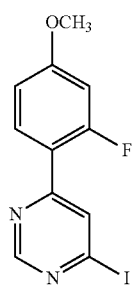 [SMILES: COc1ccc(-c2cc(I)ncn2)c(F)c1]

The compound was prepared according to Example 1 using 2-fluoro-4-methoxyphenylboronic acid and 4,6-dichloropyrimidine. The resultant chloro compound was converted to iodo with hydroiodic acid as described in the general procedure.

$^1$H NMR (DMSO-d$_6$): δ 8.91 (s, 1H), 8.23 (s, 1H), 8.05 (m, 1H), 7.01 (m, 2H), 3.88 (s, 3H).

Example 4

4-Iodo-6-(2-fluorophenyl)pyrimidine (ACT-MIF-003)

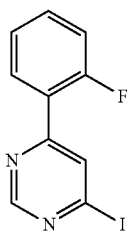

The compound was prepared according to Example 1. Specifically, the following method was employed:

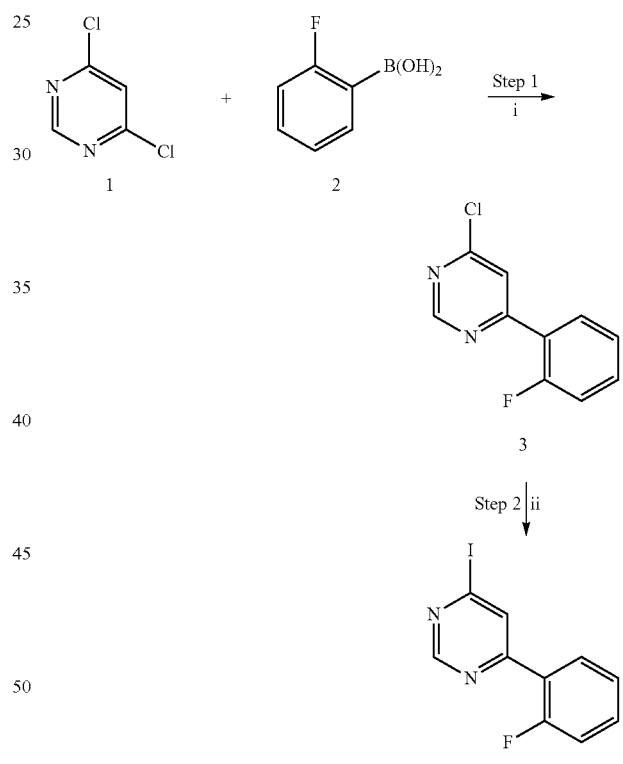

i. Pd(PPh$_3$)$_2$Cl$_2$, Na$_2$CO$_3$, DME, H$_2$O, reflux, ii. NaI, HI, acetone, 25° C.

1. Preparation of 4-chloro-6-(2-fluoro-phenyl)-pyrimidine (3) (TRM/AP/005/127)

4,6-dichloropyrimidine (20.3 g, 136.3 mmol), 2-fluorophenyl boronic acid (20.0 g, 142.9 mmol, 1.05 equiv), Na$_2$CO$_3$ (23.4 g, 106.0 mmol, 1.8 equiv) and Pd(PPh$_3$)$_2$Cl$_2$ (1.0 g, 1.4 mmol, 0.01 equiv) were refluxed in dimethoxyethane-water (817:272 mL) mixed solvent system for 6.5 h. Reaction was monitored by TLC (using ethyl acetate:n-hexane, 1:9). Reaction mixture was cooled and the subject compound was extracted using dichloromethane. Subject compound was purified by flash chromatography (2.5% ethyl acetate:n-hexane) to yield 4.5 g (Yield=15.8%).

$^1$H NMR (CDCl$_3$): 9.07 (s, 1H), 8.19 (t, J=7.8 Hz, 1H), 7.91 (s, 1H), 7.48-7.55 (m, 1H), 7.18-7.35 (m, 2H)

4,6-dichloropyrimidine (5.1 g, 34.1 mmol), 2-fluorophenyl boronic acid (5.0 g, 35.7 mmol, 1.05 equiv), Na$_2$CO$_3$ (6.9 g, 65.0 mmol, 1.8 equiv) and Pd(PPh$_3$)$_2$Cl$_2$ (0.3 g, 0.4 mmol, 0.01 equiv) were refluxed in dimethoxyethane-water (204:69 mL) mixed solvent system for 4 h. Reaction was monitored by tlc (using ethyl acetate-hexane, 1:9). Reaction mixture was cooled and the subject compound was extracted using dichloromethane. Subject compound was purified by flash chromatography (2.5% ethyl acetate in n-hexane) to yield 3.7 g (Yield=52.0%).

2. Preparation of 4-(2-fluoro-phenyl)-6-iodo-pyrimidine (4) (TRM/AP/006/064)

A solution of 4-chloro-6-(2-fluoro-phenyl)-pyrimidine (7.0 g, 33.6 mmol) in 350 mL acetone was charged with sodium iodide (25.9 g, 172.8 mmol, 5.1 equiv) and aqueous solution of HI (241.9 g, 1.9 mol, 56.4 equiv) and stirred continually for 15 h. Reaction mixture was then made slightly alkaline (pH~10) by using 5% NaOH solution. Subject compound was precipitated out, filtered, washed well with distilled water and dried under vacuum to yield 10.0 g of 4 (Yield=99.3%).

$^1$H NMR (DMSO-d$_6$): 9.02 (s, 1H), 8.35 (s, 1H), 8.01-8.07 (m, 1H), 7.60-7.65 (m, 1H), 7.38-7.44 (m, 2H)

HPLC=98.55%

Example 5

4-Iodo-6-(4-fluorophenyl)pyrimidine (ACT-MIF-004)

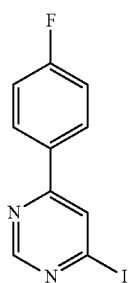

The compound was prepared according to Example 1 using 4-fluorophenylboronic acid and 4,6-dichloropyrimidine. The resultant chloro compound was converted to iodo with hydroiodic acid as described in the general procedure.

$^1$H NMR (DMSO-d$_6$): δ 8.90 (s, 1H), 8.61 (s, 1H), 8.30 (m, 2H), 7.38 (m, 2H).

Example 6

4-Iodo-6-(furan-3-yl)pyrimidine (ACT-MIF-005)

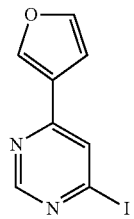 [SMILES: Ic1cc(-c2ccoc2)ncn1]

The compound was prepared according to Example 1 using furan-3-boronic acid and 4,6-dichloropyrimidine. The resultant chloro compound was converted to iodo with hydroiodic acid as described in the general procedure.

$^1$H NMR (DMSO-d$_6$): δ 8.79 (s, 1H), 8.60 (s, 1H), 8.39 (s, 1H), 7.85 (s, 1H), 7.15 (s, 1H).

Example 7

4-Iodo-6-(pyridin-3-yl)pyrimidine (ACT-MIF-006)

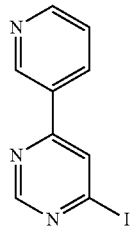 [SMILES: Ic1cc(-c2cccnc2)ncn1]

The compound was prepared according to Example 1 using pyridine-3-boronic acid and 4,6-dichloropyrimidine. The resultant chloro compound was converted to iodo with hydroiodic acid as described in the general procedure.

$^1$H NMR (DMSO-d$_6$): δ 9.40 (s, 1H), 8.96 (s, 1H), 8.72 (m, 2H), 8.53 (m, 1H), 7.52 (m, 1H).

Example 8

4-Iodo-6-(3-fluorophenyl)pyrimidine (ACT-MIF-008)

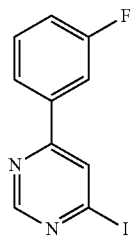 [SMILES: Fc1cccc(-c2cc(I)ncn2)c1]

The compound was prepared according to Example 1 using 3-fluorophenylboronic acid and 4,6-dichloropyrimidine. The resultant chloro compound was converted to iodo with hydroiodic acid as described in the general procedure.

$^1$H NMR (DMSO-d$_6$): δ 8.95 (s, 1H), 8.70 (s, 1H), 8.10 (m, 2H), 7.65 (m, 1H), 7.45 (m, 1H).

Example 9

4-Iodo-6-(4-tert-butyloxymethylphenyl)pyrimidine (ACT-MIF-010)

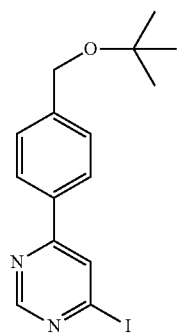 [SMILES: CC(C)(C)OCc1ccc(-c2cc(I)ncn2)cc1]

The compound was prepared according to Example 1 using 4-tert-butyloxymethylphenylboronic acid and 4,6-dichloropyrimidine. The resultant chloro compound was converted to iodo with hydroiodic acid as described in the general procedure.

$^1$H NMR (CDCl$_3$): δ 8.8 (s, 1H), 8.10 (s, 1H), 7.98 (m, 2H), 7.42 (m, 2H), 4.71 (s, 2H), 1.50 (s, 9H).

Example 10

4-Iodo-6-(2-fluoropyridin-3-yl)pyrimidine (ACT-MIF-011)

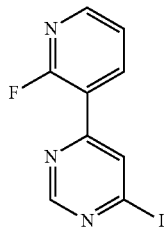

The compound was prepared according to Example 1 using 2-fluoropyridine-3-boronic acid and 4,6-dichloropyrimidine. The resultant chloro compound was converted to iodo with hydroiodic acid as described in the general procedure.

$^1$H NMR (DMSO-d$_6$): δ 8.94 (s, 1H), 8.70 (m, 1H), 8.40 (s, 1H), 7.69 (s, 1H), 7.42 (m, 1H).

Example 11

4-Iodo-6-(furan-2-yl)pyrimidine (ACT-MIF-012)

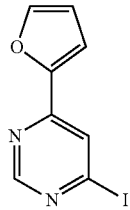 [SMILES: Ic1cc(-c2ccco2)ncn1]

The compound was prepared according to Example 1 using furan-2-boronic acid and 4,6-dichloropyrimidine. The resultant chloro compound was converted to iodo with hydroiodic acid as described in the general procedure.

$^1$H NMR (DMSO-d$_6$): δ 8.80 (s, 1H), 8.22 (s, 1H), 8.01 (s, 1H), 7.50 (s, 1H), 6.79 (s, 1H).

Example 12

4-Iodo-6-(4-fluoropyrimidin-3-yl)pyrimidine (ACT-MIF-013)

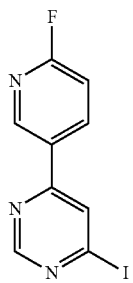

The compound was prepared according to Example 1 using 2-fluoropyridine-5-boronic acid and 4,6-dichloropyrimidine. The resultant chloro compound was converted to iodo with hydroiodic acid as described in the general procedure.

$^1$H NMR (CDCl$_3$): δ 8.71 (s, 1H), 8.39 (s, 1H), 8.25 (s, 1H), 8.15 (m, 1H), 6.50 (m, 1H).

Example 13

4-Iodo-6-(3-fluoro-4-methoxyphenyl)pyrimidine (ACT-MIF-014)

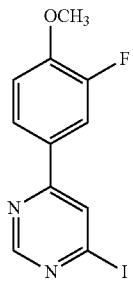 [SMILES: COc1ccc(-c2cc(I)ncn2)cc1F]

The compound was prepared according to Example 1 using 3-fluoro-4-methoxyphenylboronic acid and 4,6-dichloropyrimidine. The resultant chloro compound was converted to iodo with hydroiodic acid as described in the general procedure.

$^1$H NMR (CDCl$_3$): δ 8.89 (s, 1H), 8.60 (s, 1H), 8.12 (m, 2H), 7.31 (m, 1H), 3.92 (s, 3H).

Example 14

4-Iodo-6-(2-chloropyridin-5-yl)pyrimidine (ACT-MIF-015)

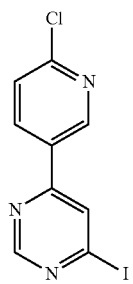 [SMILES: Clc1ccc(-c2cc(I)ncn2)cn1]

The compound was prepared according to Example 1 using 2-chloropyridine-5-boronic acid and 4,6-dichloropyrimidine. The resultant chloro compound was converted to iodo with hydroiodic acid as described in the general procedure.

¹H NMR (DMSO-d₆): δ 9.20 (m, 1H), 9.0 (s, 1H), 8.70 (s, 1H), 8.60 (m, 1H), 7.72 (m, 1H).

Example 15

4-Iodo-6-(2-hydroxyphenyl)pyrimidine
(ACT-MIF-016)

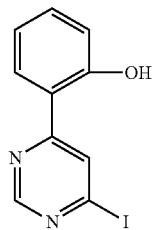 [SMILES: Oc1ccccc1-c1cc(I)ncn1]

The compound was prepared according to Example 1 using 2-trifluoromethoxyphenylboronic acid and 4,6-dichloropyrimidine. The resultant chloro compound was converted to iodo with hydroiodic acid as described in the general procedure.

¹H NMR (DMSO-d₆): δ 12.70 (s, 1H), 8.31 (s, 1H), 7.80 (m, 1H), 7.55 (m, 3H), 6.61 (s, 1H).

Example 16

4-Iodo-6-(2,4-difluorophenyl)pyrimidine
(ACT-MIF-017)

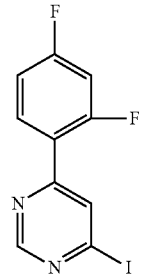

The compound was prepared according to Example 1 using 2,4-difluorophenylboronic acid and 4,6-dichloropyrimidine. The resultant chloro compound was converted to iodo with hydroiodic acid as described in the general procedure.

¹H NMR (DMSO-d₆): δ 9.01 (s, 1H), 8.39 (s, 1H), 7.80 (m, 1H), 7.41 (m, 2H).

Example 17

4-Iodo-6-(2-fluoro-6-methoxyphenyl)pyrimidine
(ACT-MIF-018)

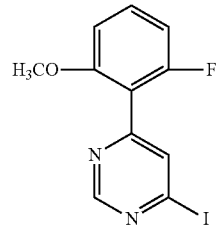 [SMILES: COc1cccc(F)c1-c1cc(I)ncn1]

The compound was prepared according to Example 1 using 2-fluoro-6-methoxyphenylboronic acid and 4,6-dichloropyrimidine. The resultant chloro compound was converted to iodo with hydroiodic acid as described in the general procedure.

¹H NMR (DMSO-d₆): δ 8.89 (s, 1H), 8.15 (s, 1H), 7.49 (m, 1H), 7.0 (m, 2H).

Example 18

4-Iodo-6-(2-chlorophenyl)pyrimidine
(ACT-MIF-019)

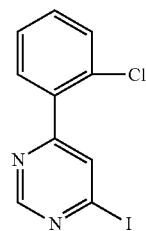

The compound was prepared according to Example 1 using 2-chlorophenylboronic acid and 4,6-dichloropyrimidine. The resultant chloro compound was converted to iodo with hydroiodic acid as described in the general procedure.

1H NMR (DMSO-d₆): δ 9.0 (s, 1H), 8.31 (s, 1H), 7.67 (m, 2H), 7.57 (m, 2H).

Example 19

4-Iodo-6-(3-acetylaminophenyl)pyrimidine
(ACT-MIF-021)

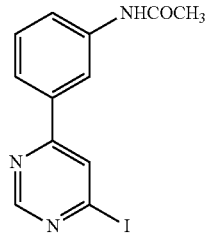

The compound was prepared according to Example 1 using 3-acetylaminophenylboronic acid and 4,6-dichloropyrimidine. The resultant chloro compound was converted to iodo with hydroiodic acid as described in the general procedure.

¹H NMR (DMSO-d₆): δ 10.15 (s, 1H), 9.10 (s, 1H), 8.50 (s, 1H), 8.25 (s, 1H), 7.90 (m, 2H), 7.55 (m, 1H), 2.10 (s, 3H).

Example 20

4-Iodo-6-(thiophen-3-yl)pyrimidine (ACT-MIF-022)

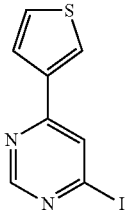 [SMILES: Ic1cc(-c2ccsc2)ncn1]

The compound was prepared according to Example 1 using thiophene-3-boronic acid and 4,6-dichloropyrimidine. The resultant chloro compound was converted to iodo with hydroiodic acid as described in the general procedure.

¹H NMR (DMSO-d₆): δ 8.88 (s, 1H), 8.58 (s, 1H), 8.50 (s, 1H), 7.88 (m, 1H), 7.71 (m, 1H).

Example 21

4-Iodo-6-(3-hydroxymethylphenyl)pyrimidine (ACT-MIF-023)

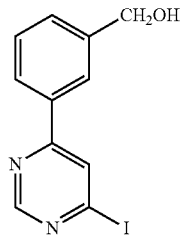 [SMILES: OCc1cccc(-c2cc(I)ncn2)c1]

The compound was prepared according to Example 1 using 3-tert-butyloxymethylphenylboronic acid and 4,6-dichloropyrimidine. The resultant chloro compound was converted to iodo with hydroiodic acid as described in the general procedure.

¹H NMR (DMSO-d₆): δ 8.92 (s, 1H), 8.58 (s, 1H), 8.22 (m, 1H), 8.19 (m, 1H), 7.50 (m, 2H), 4.60 (s, 2H).

Example 22

4-Iodo-6-(isoquinolin-4-yl)pyrimidine (ACT-MIF-025)

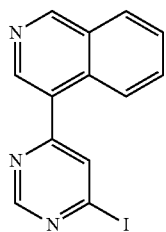 [SMILES: Ic1cc(-c2cncc3ccccc23)ncn1]

The compound was prepared according to Example 1 using isoquinoline-4-boronic acid and 4,6-dichloropyrimidine. The resultant chloro compound was converted to iodo with hydroiodic acid as described in the general procedure.

¹H NMR (DMSO-d₆): δ 9.69 (s, 1H), 9.30 (m, 1H), 9.05 (s, 1H), 8.90 (s, 1H), 8.15 (m, 2H), 7.90 (m, 1H), 7.70 (m, 1H).

Example 23

4-Iodo-6-(2,4,5-trifluorophenyl)pyrimidine (ACT-MIF-027)

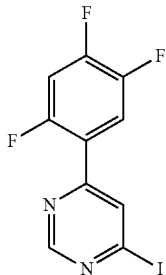 [SMILES: Fc1cc(F)c(-c2cc(I)ncn2)cc1F]

The compound was prepared according to Example 1 using 2,4,5-trifluorophenylboronic acid and 4,6-dichloropyrimidine. The resultant chloro compound was converted to iodo with hydroiodic acid as described in the general procedure.

¹H NMR (DMSO-d₆): δ 9.0 (s, 1H), 8.32 (s, 1H), 8.12 (m, 1H), 7.81 (m, 1H).

Example 24

4-Iodo-6-(2,4-difluoropyridin-3-yl)pyrimidine (ACT-MIF-028)

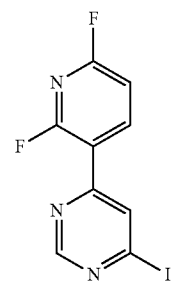

The compound was prepared according to Example 1 using 2,6-difluoropyridine-3-boronic acid and 4,6-dichloropyrimidine. The resultant chloro compound was converted to iodo with hydroiodic acid as described in the general procedure.

¹H NMR (DMSO-d₆): δ 9.05 (s, 1H), 8.75 (m, 1H), 8.36 (s, 1H), 7.40 (m, 1H).

Example 25

4-Iodo-6-(4-methoxypyridin-3-yl)pyrimidine (ACT-MIF-029)

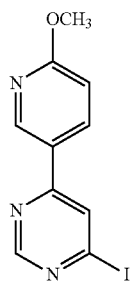 [SMILES: COc1ccc(-c2cc(I)ncn2)cn1]

The compound was prepared according to Example 1 using 2-methoxypyridine-5-boronic acid and 4,6-dichloropyrimidine. The resultant chloro compound was converted to iodo with hydroiodic acid as described in the general procedure.

¹H NMR (DMSO-d₆): δ 9.10 (d, 1H), 8.90 (s, 1H), 8.61 (s, 1H), 8.45 (m, 1H), 7.0 (m, 1H), 3.92 (s, 3H).

Example 26

4-Iodo-6-(thiophen-2-yl)pyrimidine (ACT-MIF-030)

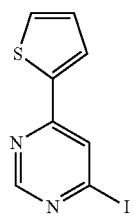 [SMILES: Ic1cc(-c2cccs2)ncn1]

The compound was prepared according to Example 1. Specifically, the following method was employed:

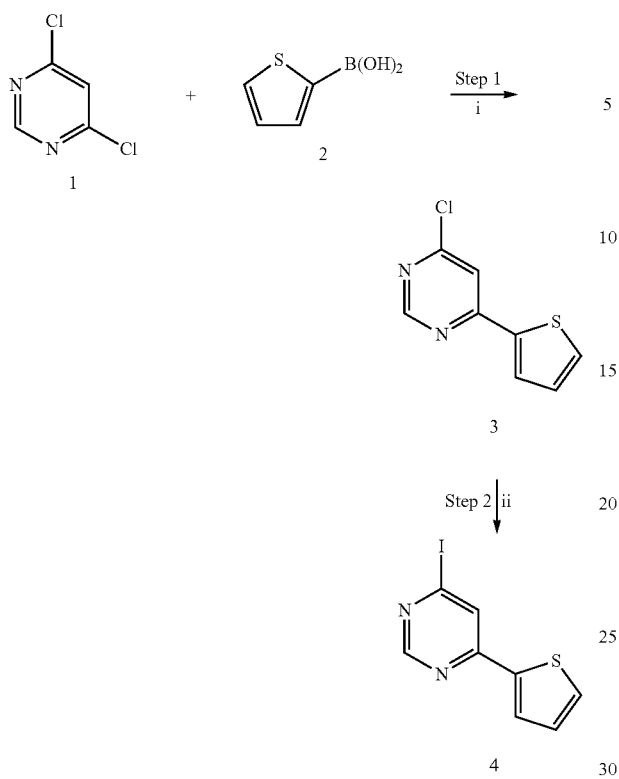

i. Pd(PPh₃)₂Cl₂, Na₂CO₃, DME, H₂O, reflux. ii. HI, 25° C.

1. Preparation of 4-chloro-6-thiophen-2-yl-pyrimidine (3)

4,6-dichloropyrimidine (22.2 g, 149.1 mmol), thiophene-2-boronic acid (20.0 g, 156.3 mmol, 1.05 equiv), Na₂CO₃ (28.8 g, 271.4 mmol, 1.8 equiv) and Pd(PPh₃)₂Cl₂ (2.9 g, 4.2 mmol, 0.03 equiv) were refluxed in dimethoxyethane-water (727:238 mL) mixed solvent system for 16 h. Reaction was monitored by TLC (using ethyl acetate:n-hexane, 1:9). Reaction mixture was cooled and the subject compound was extracted using dichloromethane. Subject compound was purified by flash chromatography (5% ethyl acetate:n-hexane) to yield 18.4 g of 3 (Yield=62.8%).
¹H NMR (CDCl₃): 8.90 (d, J=0.9 Hz 1H), 7.79-7.80 (dd, J=3.9, 1.2 Hz, 1H), 7.58-7.60 (m, 2H), 7.18-7.20 (m, 1H).

2. Preparation of 4-iodo-6-thiophen-2-yl-pyrimidine (4)

Aqueous solution of HI (63.5 g, 496.5 mol, 13.9 equiv) was charged to 4-chloro-6-thiophen-2-yl-pyrimidine (3, 7.0 g, 35.6 mmol) and stirring was continued for 20 h. Reaction mixture was then made slightly alkaline (pH~10) by using 5% NaOH solution. Subject compound was precipitated out, filtered, washed well with distilled water and dried under vacuum to yield 9.6 g of 4 (Yield=94.1%).
HPLC=93.1%
To convert the unreacted chloro-, the product was again treated with HI (6.1 g, 47.7 mmol, 13.9 equiv) by following the same procedure as mentioned above to get 10.0 g of 4 (Yield=98.0%).
¹H NMR (CDCl₃): 8.76 (s, 1H), 8.02 (s, 1H), 7.76 (d, J=3.9 Hz, 1H), 7.58 (d, J=4.8 Hz, 1H), 7.16-7.19 (m, 2H).
HPLC=99.12%

Example 27

4-Iodo-6-(3,4-difluorophenyl)pyrimidine (ACT-MIF-032)

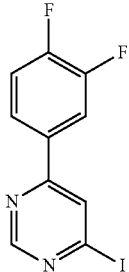

The compound was prepared according to Example 1 using 3,4-difluorophenylboronic acid and 4,6-dichloropyrimidine. The resultant chloro compound was converted to iodo with hydroiodic acid as described in the general procedure.
¹H NMR (DMSO-d₆): δ 8.94 (s, 1H), 8.69 (s, 1H), 8.31 (m, 1H), 8.13 (m, 1H), 7.68 (m, 1H).

Example 28

4-Iodo-6-(4-ethoxyphenyl)pyrimidine (ACT-MIF-033)

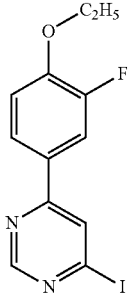 [SMILES: CCOc1ccc(-c2cc(I)ncn2)cc1F]

The compound was prepared according to Example 1 using 3-fluoro-4-ethoxyphenylboronic acid and 4,6-dichloropyrimidine. The resultant chloro compound was converted to iodo with hydroiodic acid as described in the general procedure.
¹H NMR (DMSO-d₆): δ 8.89 (s, 1H), 8.60 (s, 1H), 8.05 (m, 1H), 7.21 (m, 2H), 4.20 (m, 2H), 1.32 (m, 3H).

Example 29

4-Iodo-6-(4-aminocarbonylphenyl)pyrimidine (ACT-MIF-034)

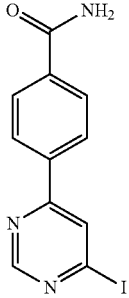 [SMILES: NC(=O)c1ccc(-c2cc(I)ncn2)cc1]

The compound was prepared according to Example 1 using 4-aminocarbamoylphenylboronic acid and 4,6-dichloropyrimidine. The resultant chloro compound was converted to iodo with hydroiodic acid as described in the general procedure.

$^1$H NMR (DMSO-d$_6$): δ 8.99 (s, 1H), 8.7 (s, 1H), 8.30 (m, 2H), 8.12 (s, 1H), 8.0 (m, 2H), 7.51 (s, 1H).

Example 30

4-Iodo-6-(3-aminocarbonylphenyl)pyrimidine (ACT-MIF-035)

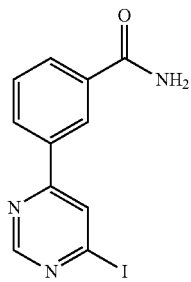 [SMILES: NC(=O)c1cccc(-c2cc(I)ncn2)c1]

The compound was prepared according to Example 1 using 3-aminocarbamoylphenylboronic acid and 4,6-dichloropyrimidine. The resultant chloro compound was converted to iodo with hydroiodic acid as described in the general procedure.

$^1$H NMR (DMSO-d$_6$): δ 8.95 (s, 1H), 8.65 (m, 2H), 8.40 (m, 1H), 8.19 (s, 1H), 8.08 (m, 1H), 7.62 (m, 2H).

Example 31

4-Iodo-6-(quinolin-4-yl)pyrimidine (ACT-MIF-036)

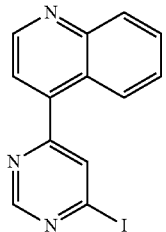 [SMILES: Ic1cc(-c2ccnc3ccccc23)ncn1]

The compound was prepared according to Example 1 using quinoline-4-boronic acid and 4,6-dichloropyrimidine. The resultant chloro compound was converted to iodo with hydroiodic acid as described in the general procedure.

$^1$H NMR (DMSO-d$_6$): δ 9.11 (s, 1H), 9.0 (s, 1H), 8.47 (s, 1H), 8.12 (m, 2H), 7.81 (m, 1H), 7.7 (s, 1H), 7.61 (m, 1H).

Example 32

4-Iodo-6-(quinolin-8-yl)pyrimidine

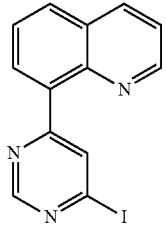 [SMILES: Ic1cc(-c2cccc3cccnc23)ncn1]

The compound was prepared according to Example 1 using quinolin-8-boronic acid and 4,6-dichloropyrimidine. The resultant chloro compound was converted to iodo with hydroiodic acid as described in the general procedure.

$^1$H NMR (DMSO-d$_6$): δ 8.80 (s, 1H), 8.49 (m, 1H), 8.30 (s, 1H), 7.98 (m, 1H), 7.88 (s, 1H), 7.62 (m, 2H), 7.52 (m, 1H).

Example 33

4-Iodo-6-(quinolin-3-yl)pyrimidine

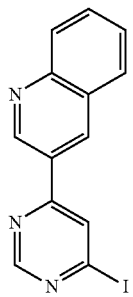 [SMILES: Ic1cc(-c2cnc3ccccc3c2)ncn1]

The compound was prepared according to Example 1 using quinolin-3-boronic acid and 4,6-dichloropyrimidine. The resultant chloro compound was converted to iodo with hydroiodic acid as described in the general procedure.

$^1$H NMR (DMSO-d$_6$): δ 9.65 (s, 1H), 9.23 (s, 1H), 9.01 (s, 1H), 8.87 (s, 1H), 8.01 (m, 2H), 7.90 (m, 1H), 7.66 (m, 1H).

Example 34

4-Iodo-6-(isoquinolin-5-yl)pyrimidine

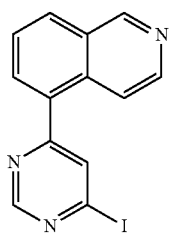 [SMILES: Ic1cc(-c2cccc3cnccc23)ncn1]

The compound was prepared according to Example 1 using isoquinolin-5-boronic acid and 4,6-dichloropyrimidine. The resultant chloro compound was converted to iodo with hydroiodic acid as described in the general procedure.

$^1$H NMR (DMSO-d$_6$): δ 9.41 (s, 1H), 9.09 (s, 1H), 8.51 (m, 1H), 8.42 (s, 1H), 8.30 (m, 1H), 8.10 (m, 2H), 7.80 (m, 1H).

Example 35

Methods for the preparation of 2-alkylthio derivatives

Scheme 2

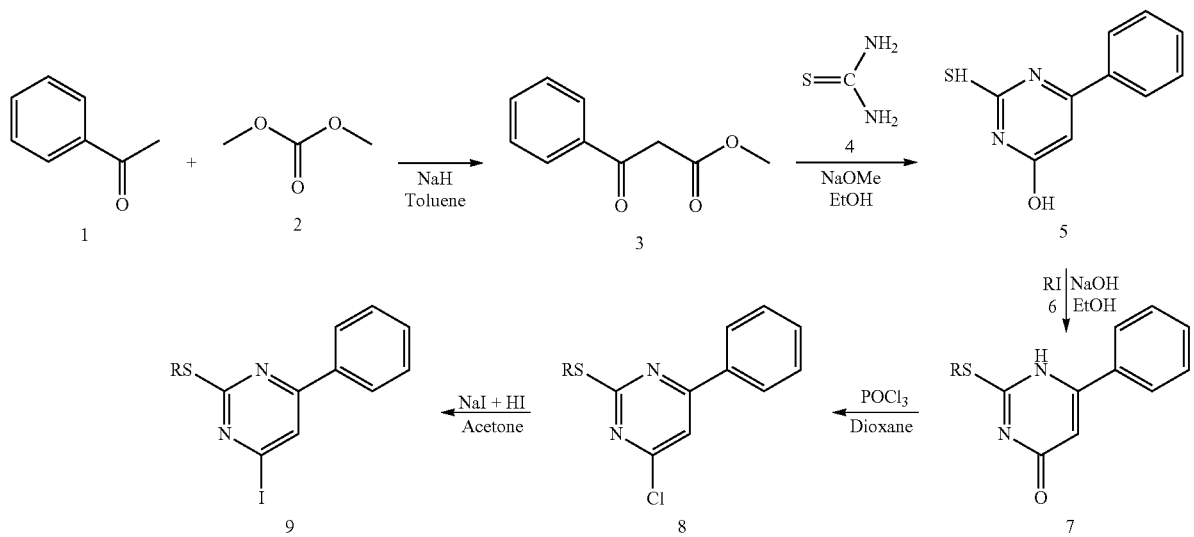

The compounds of Examples 36-39 are prepared using the method of Example 35.

Example 36

2-Methylthio-4-iodo-6-phenylpyrimidine

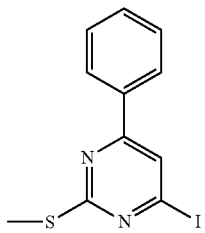

The compound was prepared according to Example 35 using methyl iodide as one of the reactants.

$^1$H NMR (CDCl$_3$): δ 8.03-8.06 (m, 2H), 7.82 (s, 1H), 7.49-7.54 (m, 3H), 2.62 (s, 3H).

Example 37

2-Ethylthio-4-iodo-6-phenylpyrimidine

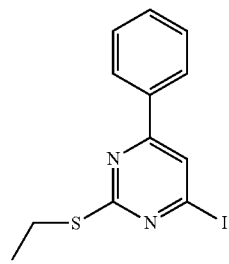 [SMILES: CCSc1nc(I)cc(-c2ccccc2)n1]

The compound was prepared according to Example 35 using ethyl iodide as one of the reactants.

$^1$H NMR (CDCl$_3$): δ 7.95-7.96 (m, 2H), 7.74 (s, 1H), 7.39-7.48 (m, 3H), 3.14 (q, J=7.2 Hz, 2H), 1.38 (t, J=7.2 Hz, 3H).

Example 38

2-Isopropylthio-4-iodo-6-phenylpyrimidine

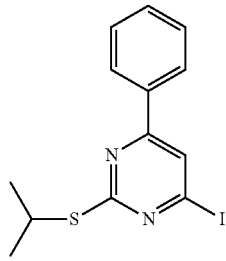 [SMILES: CC(C)Sc1nc(I)cc(-c2ccccc2)n1]

The compound was prepared according to Example 35 using isopropyl iodide as one of the reactants.

$^1$H NMR (DMSO-d$_6$): δ 8.25 (s, 1H), 8.17-8.20 (m, 2H), 7.51-7.59 (m, 3H), 3.89-3.99 (h, J=6.9 Hz, 1H), 1.42 (d, J=6.9 Hz, 6H).

Example 39

2-n-Butylthio-4-iodo-6-phenylpyrimidine

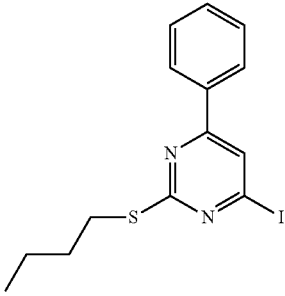 [SMILES: CCCCSc1nc(I)cc(-c2ccccc2)n1]

The compound was prepared according to Scheme-2 using n-butyl iodide as one of the reactant.

¹H NMR (DMSO-d₆): δ 8.26 (s, 1H), 8.18-8.20 (m, 2H), 7.54-7.59 (m, 3H), 3.18 (t, J=7.2 Hz, 2H), 1.65-1.73 (m, J=7.2 Hz, 2H), 1.41-1.49 (m, J=7.2 Hz, 2H), 0.93 (t, J=7.2 Hz, 3H).

Example 40

Methods for the preparation of 2-alkylamino derivatives

Example 42

2-Ethylamino-4-iodo-6-phenylpyrimidine

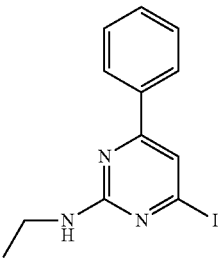

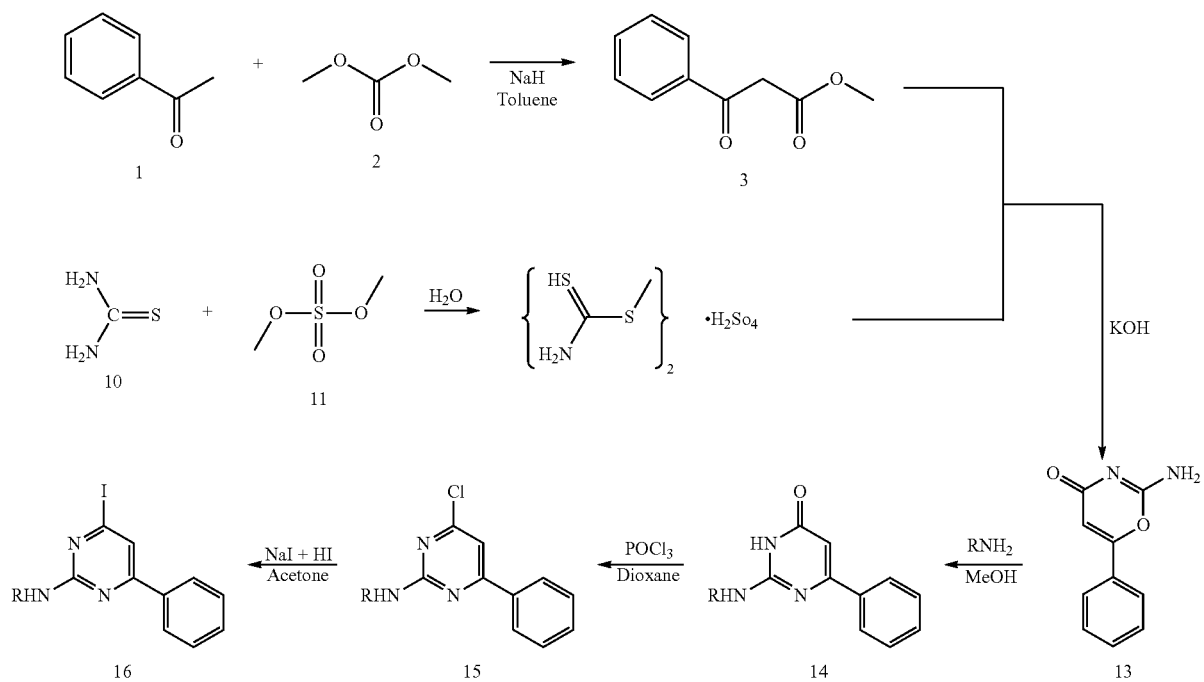

Scheme 3

The compounds of Examples 41-45 were prepared according to Scheme 3 of Example 40.

Example 41

2-Methylamino-4-iodo-6-phenylpyrimidine

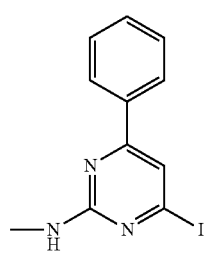

The compound was prepared according to Example 40 using methylamine as RNH₂.

¹H NMR (CDCl₃): δ 7.98-8.00 (br s, 2H), 7.43-7.49 (m, 3H), 7.40 (s, 1H), 5.24 (br s, 1H), 3.06 (d, J=3.0 Hz).

The compound was prepared according to Example 40 using ethylamine as RNH₂.

¹H NMR (CDCl₃): δ 7.97-7.99 (m, 2H), 7.44-7.48 (m, 3H), 7.39 (s, 1H), 5.20 (br s, 1H), 3.48-3.57 (m, J=7.2 Hz, 1.2 Hz, 2H), 1.28 (t, J=7.2 Hz, 3H).

Example 43

2-Propylamino-4-iodo-6-phenylpyrimidine

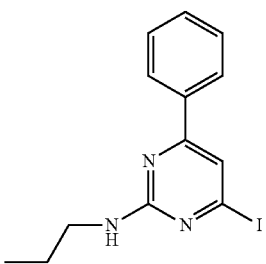 [SMILES: CCCNc1nc(I)cc(-c2ccccc2)n1]

The compound was prepared according to Example 40 using propylamine as RNH₂.

¹H NMR (CDCl₃): δ 7.92 (br s, 2H), 7.35-7.44 (m, J=6.6 Hz, 3H), 7.31 (s, 1H), 5.21 (br s, 1H), 3.38 (q, J=6.9 Hz, 2H), 1.53-1.65 (m, J=6.9, 7.3 Hz, 2H), 0.93 (t, J=7.3 Hz, 3H).

Example 44

2-Isopropylamino-4-iodo-6-phenylpyrimidine

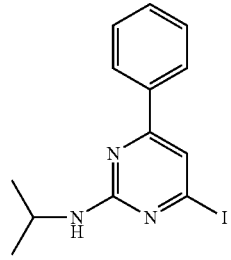 [SMILES: CC(C)Nc1nc(I)cc(-c2ccccc2)n1]

The compound was prepared according to Example 40 using isopropylamine as RNH₂.

¹H NMR (CDCl₃): δ 8.04-8.07 (m, 2H), 7.54-7.56 (m, 3H), 7.41 (s, 1H), 6.98 (br s, 1H), 4.29-4.36 (m, J=6.9, 3.3 Hz, 1H), 1.34 (d, J=6.9, 6H).

Example 45

2-n-Butylamino-4-iodo-6-phenylpyrimidine

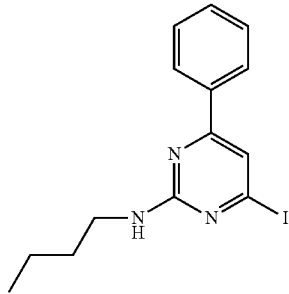 [SMILES: CCCCNc1nc(I)cc(-c2ccccc2)n1]

The compound was prepared according to Example 40 using n-butylamine as RNH₂.

¹H NMR (CDCl₃): δ 7.97 (br s, 2H), 7.45-7.48 (m, 3H), 7.38 (s, 1H), 5.30 (br s, 1H), 1.57-1.64 (m, J=6.0 Hz, 2H), 1.40-1.47 (h, J=6.0, 2H), 0.96 (t, J=6.0 Hz, 3H).

The compounds of Examples 46-56 are also prepared according the Scheme 1.

Example 46

4-Iodo-6-(benzothiophen-2-yl)pyrimidine

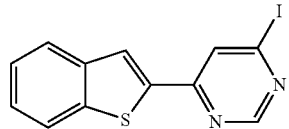 [SMILES: Ic1cc(-c2cc3ccccc3s2)ncn1]

Example 47

4-Iodo-6-(benzofuran-2-yl)pyrimidine

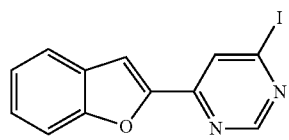 [SMILES: Ic1cc(-c2cc3ccccc3o2)ncn1]

Example 48

4-Iodo-6-(4-hydroxybenzothiophen-2-yl)pyrimidine

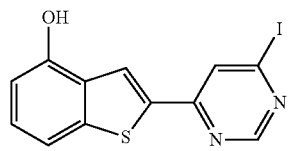 [SMILES: Oc1cccc2sc(-c3cc(I)ncn3)cc12]

Example 49

4-Iodo-6-(4-acetylaminobenzothiophen-2-yl)pyrimidine

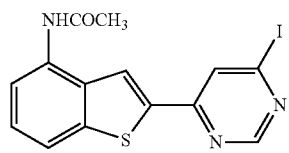

Example 50

4-Iodo-6-(4-aminocarbonylbenzothiophen-2-yl)pyrimidine

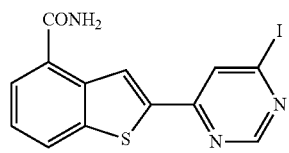 [SMILES: NC(=O)c1cccc2sc(-c3cc(I)ncn3)cc12]

Example 51

4-Iodo-6-(5-acetylaminopyridin-3-yl)pyrimidine

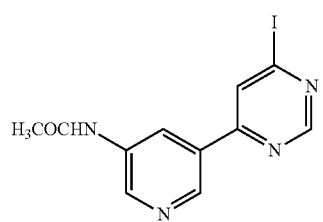

Example 52

4-Iodo-6-(5-aminocarbonylpyridin-3-yl)pyrimidine

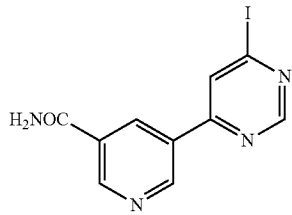 [SMILES: NC(=O)c1cncc(-c2cc(I)ncn2)c1]

Example 53

4-Iodo-6-(4-fluoropyridin-3-yl)pyrimidine

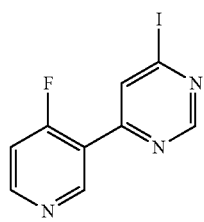 [SMILES: Fc1ccncc1-c1cc(I)ncn1]

Example 54

4-Iodo-6-(4-acetylaminothiophen-2-yl)pyrimidine

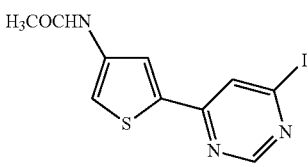

Example 55

4-Iodo-6-(4-aminocarbonylthiophen-2-yl)pyrimidine

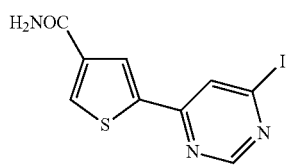 [SMILES: NC(=O)c1csc(-c2cc(I)ncn2)c1]

Example 56

4-Iodo-6-(4-methoxythiophen-2-yl)pyrimidine

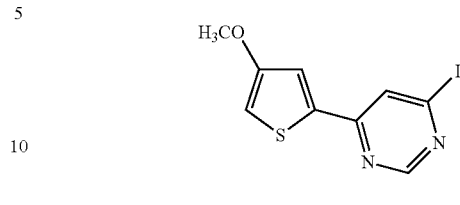

Example 57

Solubility and Stability

Solubility of exemplary compounds in varying solvents is shown in Table 2. The stability of the compounds in solution was examined by HPLC concomitantly. Results indicated no degradation after 2 months stored at room temperature.

TABLE 2

Solubilities of the compounds of the invention at 20-22 C. (mg/ml)

|  | MIF 001 | MIF 002 | MIF 003 | MIF 006 | MIF 035 | MIF 038 |
|---|---|---|---|---|---|---|
| Ethanol |  |  | 85.0 |  | 1.4 | 4.7 |
| DMSO |  |  | 216 |  | — | 150 |
| Propane-diol |  |  | 25 |  | 2.7 |  |
| PEG-300 |  |  | 66 |  | 13.3 | 19.7 |
| Corn oil |  |  | 15 |  | <6 | <6 |
| Ethanol/Tween 80 |  |  | 20 |  | 10 | 10 |
| Cremophor |  |  | 15 |  |  | 14.5 |

Example 58

Cell Permeability and Transport

Cell permeability and transport mechanisms in Caco-2 and MDR1-MDCK monolayers experiments were performed in triplicate in the apical-to-basolateral and basolateral-to-apical direction using Transwell® wells containing either Caco-2 or MDR1-MDCK monolayers. A modified Hanks buffer pH 7.4 was used in both reservoir and receiver wells with the addition of 1% BSA in the receiver side. Confluent monolayers were used and their integrity was verified using reference compounds (Atenolol as a low permeability reference compound and Propanolol as a high permeability reference compound). A sample in the basolateral and apical sides was taken after 2 hours and the concentration measured by LC/MS-MS. Results are summarized in Table 3. The results also suggest that the compounds are not P-gp substrates and may cross the blood brain barrier.

Table 3A: Cell permeability and transport results (Caco-2)

|  | Caco-2 Permeability | | | |
|---|---|---|---|---|
|  | Papp ($10^4$ cm/s) | | | Permeability |
|  | A-B | B-A | Efflux | Class |
| ACT-MIF-001 | <0.1 | <0.1 | — | Low |
| ACT-MIF-002 | 0.2 | 04 | 1.7 | Low |

-continued

| | | | | |
|---|---|---|---|---|
| ACT-MIF-003 | 2.1 | 2.6 | 1.2 | High |
| ACT-MIF-006 | 5.4 | 7.8 | 1.4 | High |
| ACT-MIF-011 | 12.6 | 7.8 | 0.6 | High |
| ACT-MIF-025 | 0.4 | 0.6 | 1.5 | Low |
| ACT-MIF-029 | 3.1 | 3.1 | 1.0 | High |
| ACT-MIF-033 | 2.7 | 3.0 | 1.1 | High |
| ACT-MIF-035 | 3.1 | 3.3 | 1.1 | High |
| ACT-MIF-038 | 0.9 | 06 | 0.7 | High |

Table 3B: Cell permeability and transport results (MDR1-MDCK)

| | MDR1-MDCK Permeability | | | | |
|---|---|---|---|---|---|
| | Papp ($10^4$ cm/s) | | | | |
| | A-B | B-A | P-gp Substrate | Efflux | Brain (1) |
| ACT-MIF-001 | 2.3 | 1.9 | No | Low | Low |
| ACT-MIF-001 + CSA | 3.3 | 3.1 | | | |
| ACT-MIF-002 | 1.0 | 0.7 | No | High | Low |
| ACT-MIF-002 + CSA | 1.9 | 2.0 | | | |
| ACT-MIF-003 | 3.3 | 3.3 | No | High | High |
| ACT-MIF-003 + CSA | 5.2 | 4.7 | | | |

(1) Brain penetration classification

Example 59

Microsomal Stability

Stability in human liver microsomes was tested over 24 hours at 37° C. using pooled mixed gender human liver microsomes. Liver microsomes were prepared at 1.0 mg/ml of microsomal protein in a 100 mM potassium phosphate pH 7.4 buffer with 1 mM NADPH. The media was incubated at 37° C. with the compound in solution in DMSO. The concentration of the compound was followed by LC/MS-MS as a function of time. Samples were assayed at t=0, 30, 60 and 120 minutes. Testosterone was used as a positive control. The same experiment was performed with mouse liver microsomes instead of human liver microsomes. Results are summarized in Table 4.

TABLE 4

Metabolic stability determined from stability in human microsomes

| | Metabolic Stability in Human Microsomes % Remaining | | |
|---|---|---|---|
| | 0 min | 15 min | 60 min |
| ACT-MIF-001 | 100 | | <2 |
| ACT-MIF-002 | 100 | | <2 |
| ACT-MIF-003 | 100 | | 57 |
| ACT-MIF-006 | 100 | | 82 |
| ACT-MIF-017 | 100 | | 0 |
| ACT-MIF-021 | 100 | | 73 |
| ACT-MIF-029 | 100 | | 6.4 |
| ACT-MIF-033 | 100 | | 82 |
| ACT-MIF-035 | 100 | | 92 |
| ACT-MIF-038 | 100 | | 47 |
| Testosterone | 100 | 56 | |

Example 60

Plasma Protein Binding

Plasma protein binding was ascertained using dialysis equilibrium methods known in the art. Results are summarized in Table 5. Warfarin was used a high protein binding control.

TABLE 5

Human plasma protein binding

| | Human Plasma Protein Binding % Bound | |
|---|---|---|
| | Compound | Warfarin |
| ACT-MIF-001 | 98.3 | 99.0 |
| ACT-MIF-002 | 97.9 | 98.9 |
| ACT-MIF-003 | 96.2 | 98.9 |

Example 61

MIF Liver Lysates Enzymatic Activity

This experiment, using an ex-vivo approach and the tautomeric reaction of L-dopachrom, was designed to ascertain the level of inhibition of MIF following administration of the compounds of this invention via oral, IV, IP or any other route of administration. Mice were used in the example illustrated below, but other animals could be used as well. Groups of 3 mice were administered IP 1 mg of 4-IPP and ACT-002 resuspended in 100 µl of corn oil every day for 3 days. Mice were sacrificed 6 hours after the last injection and livers were harvested. ~1 gram pieces of liver were lysed in PBS containing 1 mM $NaVO_4$, 2 mM NaF and a protease inhibitor cocktail (Roche Biochemical, Indianapolis, Ind.) using dounce-homogenization on ice. 500 µg of liver lysates were added to a final volume of 700 µl PBS in plastic cuvettes. 4 mM L-3,4-dihydroxyphenylalanine methyl ester and 8 mM sodium periodate (Sigma-Aldrich) were combined in a 3:2 ratio to form L-dopachrome methyl ester. 300 µL of L-dopachrome methyl ester was then immediately added to the cuvettes; the $OD_{475\ nm}$ was measured 2 min and 4 min after addition of the L-dopachrome. As shown in FIG. 1 (DMSO was used as a negative control—no inhibition of MIF), there is a significant in vivo inhibition of MIF indicating that the compound interacts with the MIF binding pocket.

Example 62

MIF Tumor Lysate Enzymatic Activity

Figure 2:
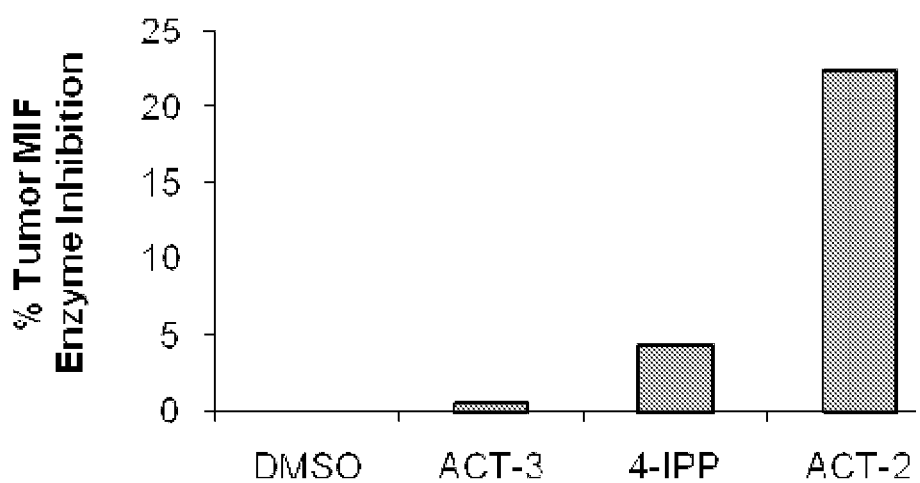
FIG. 2 depicts MIF tumor enzyme inhibition as a percent of control, comparing ACT-MIF-003, ACT-MIF-002, and 4-IPP.

The ex vivo MIF enzymatic activity of tumor extracts/lysates following in vivo dosing can be estimated in a manner similar to the method of Example 61. Tumor bearing mice were administered 1 mg/kg daily for 3 days. 6 hours following the last dose, animals were sacrificed and tumors were resected and processed as described in Example 61. Inhibition was also ascertained as in Example 61. Results, shown in FIG. 2, demonstrate significant inhibition of MIF in tumor lysates.

Example 63

Inhibition of Tumor Cells Proliferation

Figure 3:
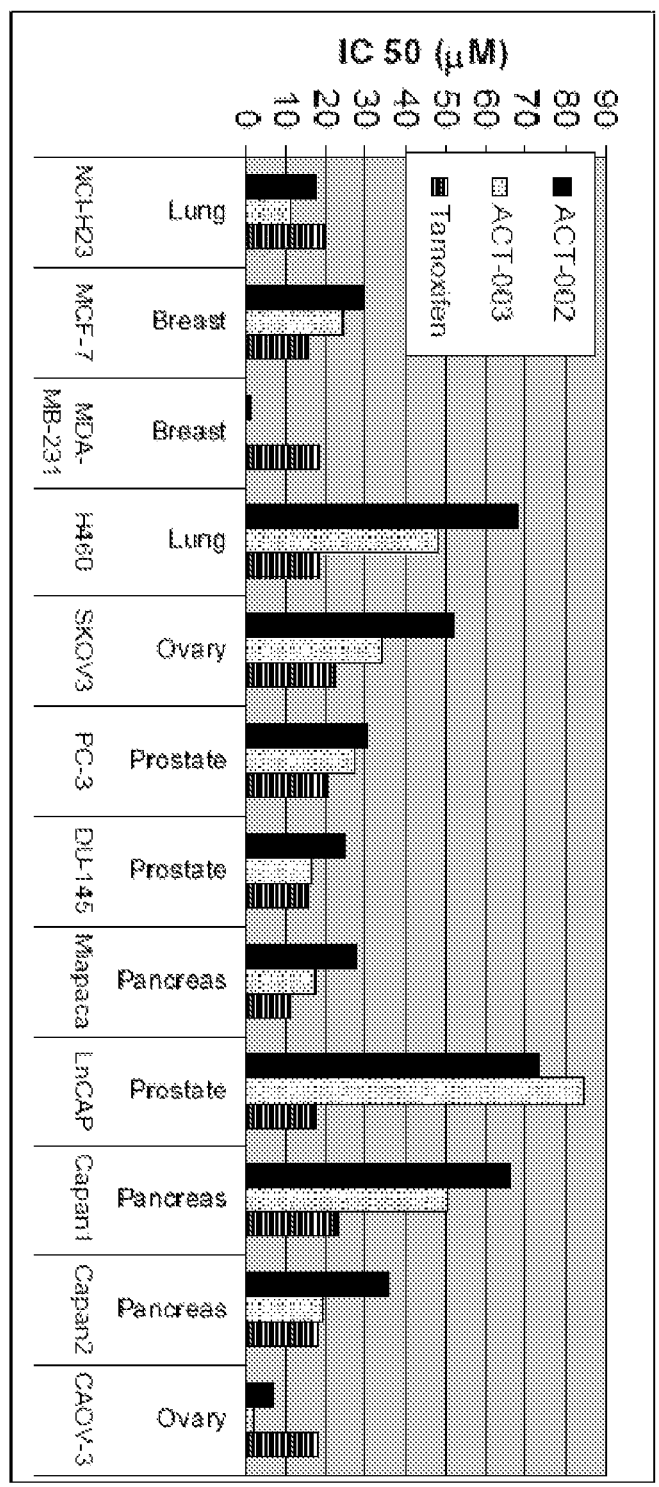
FIG. 3 depicts a comparison of IC50 values across the tumor cell lines H23, MCF7, MDA-MB-231, H-460, SKOV-3, PC3, DU145, Miapaca, LnCap, Capan 1, Capan 2, and CAOV3.
Figure 4:
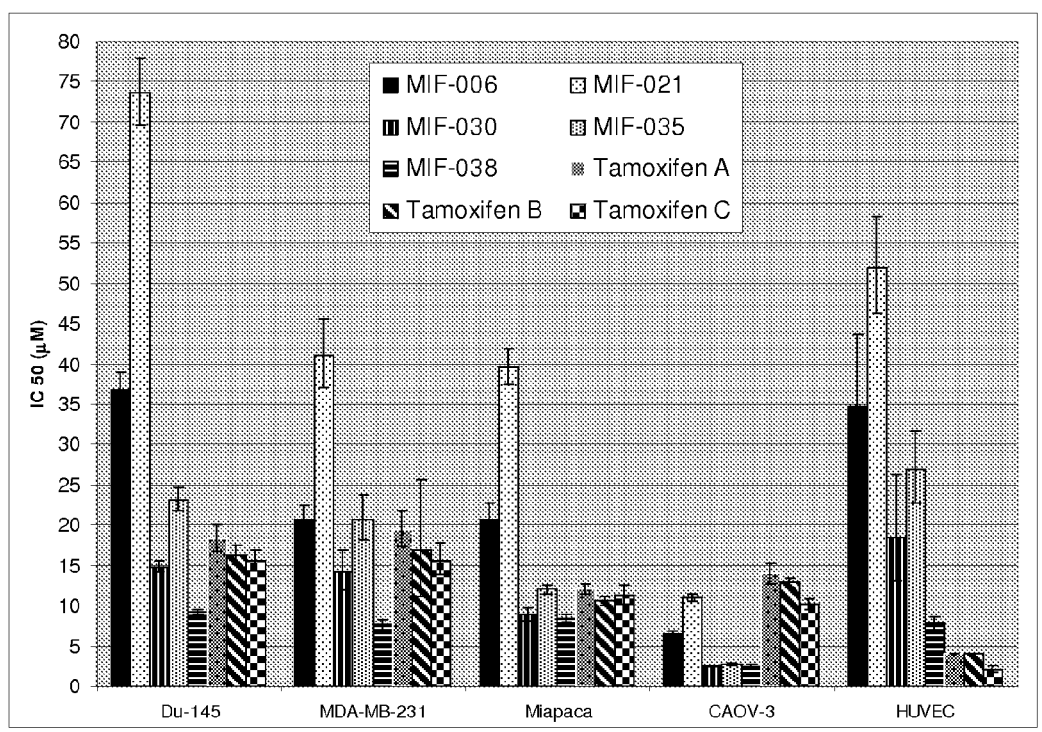
FIG. 4 depicts a comparison of IC50 values across the tumor cell lines DU145, MDA-MB-231, Miapaca, CAOV03, and HUVEC.

Inhibition of the proliferation of tumor cells was investigated in vitro in several tumor cell lines. Cells of the desired tumor cell line were plated at 2×10⁵ cells/ml in 96 well plates. Twice the indicated concentrations of the compounds of the invention were added to cells the following day in an equal volume of media. 72 hours later, cells were lysed and subjected to ATP determination using the CellTiter Glo-Luminescent Cell Viability Assay kit (Promega, Madison, Wis.). Experiments were done in triplicate. Results for the inhibition of cells proliferation are reported as IC50 (the concentration leading to a 50% inhibition of proliferation of the cell population) and are listed in Table 6. FIGS. 3 and 4 show bar graphs comparing the IC50s of specific embodiments of compounds of the invention across multiple tumor cell lines.

TABLE 6

IC50s for compounds in selected tumor cell lines.

| | IC50 (microM) Du 145 |
|---|---|
| ACT-MIF-001 | <10 |
| ACT-MIF-002 | 24.9 |
| ACT-MIF-003 | 16.5 |
| ACT-MIF-006 | 36.7 |
| ACT-MIF-017 | <10 |
| ACT-MIF-022 | <40 |
| ACT-MIF-029 | <20 |
| ACT-MIF-033 | <5 |
| ACT-MIF-034 | <100 |
| ACT-MIF-035 | 21.7 |
| ACT-MIF-038 | 9.2 |

Example 64 p53 Up Regulation

Figure 5:
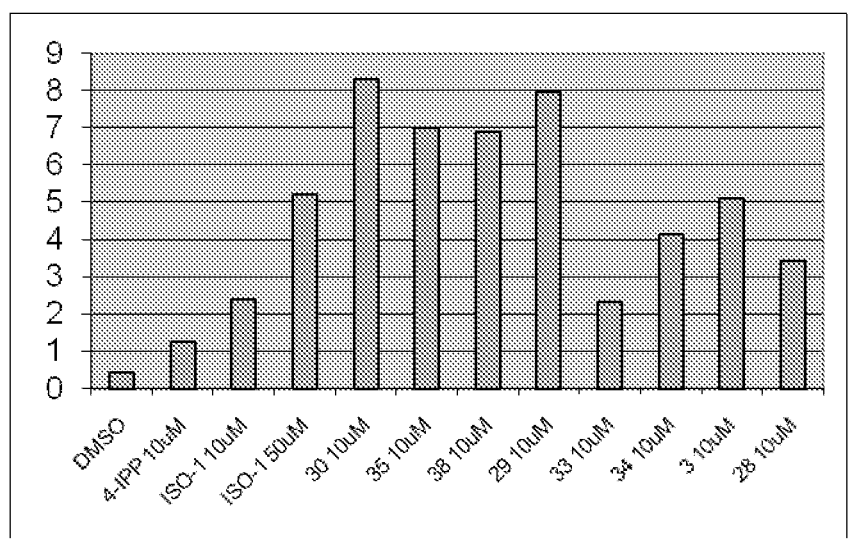
FIG. 5 depicts p53 regulation of compounds compared to control (DMSO), 4-IPP, and ISO-1 at 10 uM concentration. Compounds tested included ACT-MIF-030, ACT-MIF-035, ACT-MIF-038, ACT-MIF-029, ACT-MIF-033, ACT-MIF-034, ACT-MIF-003, and ACT-MIF-028. Results indicate the compounds are implicated in p53 regulation.

The up regulation of p53 was determined using a commercially available p53 luciferase assay kit. 1×10⁵ cells/ml were plated in a 24 well plate and allowed to adhere overnight. MIF antagonists were added to the cells at the indicated concentrations for 16 hours and transiently co-transfected with 0.125 µg/well of p53-responsive luciferase promoter plasmid (Promega, Madison, Wis.) together with 0.0125 µg/well *Renilla* pRL-null plasmid (Promega) using Lipofectamine (Invitrogen) transfection reagent. After 24 hrs, *Firefly* and *Renilla* luciferase activities were measured by the Dual Luciferase Reporter Assay System (Promega, Madison, Wis.) on a TD-20/20 luminometer (Turner Designs). Results represented in FIG. 5 indicate the compounds of the invention are implicated in p53 regulation.

Example 65

MIF Cell Lysate Enzymatic Inhibition

Normal or transformed cell lysates can be used to determine the concentration inhibiting the enzymatic activity of MIF present in cell lysates. Cells are cultured in the appropriate media to the required number of cells, collected, and lysed. Compounds to be characterized are solubilized in DMSO and serial dilutions are performed in order to obtain a range of concentrations including complete and no quantifiable inhibition. Results, reported as IC50 (concentration leading to an inhibition of 50% of the MIF enzymatic activity), are summarized in Table 7.

TABLE 7

IC50 values for MIF cell lysate enzymatic activity inhibition

| | IC50 (nM) |
|---|---|
| 4-IPP | >2000 |
| ACT-MIF-001 | 37 |
| ACT-MIF-002 | 70 |
| ACT-MIF-003 | 200 |
| ACT-MIF-006 | 250 |
| ACT-MIF-017 | 190 |
| ACT-MIF-021 | 570 |
| ACT-MIF-029 | 140 |
| ACT-MIF-033 | 115 |
| ACT-MIF-034 | 270 |
| ACT-MIF-035 | 185 |
| ACT-MIF-036 | 230 |
| ACT-MIF-037 | >1000 |
| ACT-MIF-039 | 195 |

Example 66

Inhibition of Cell Migration and Invasion

Figure 6:
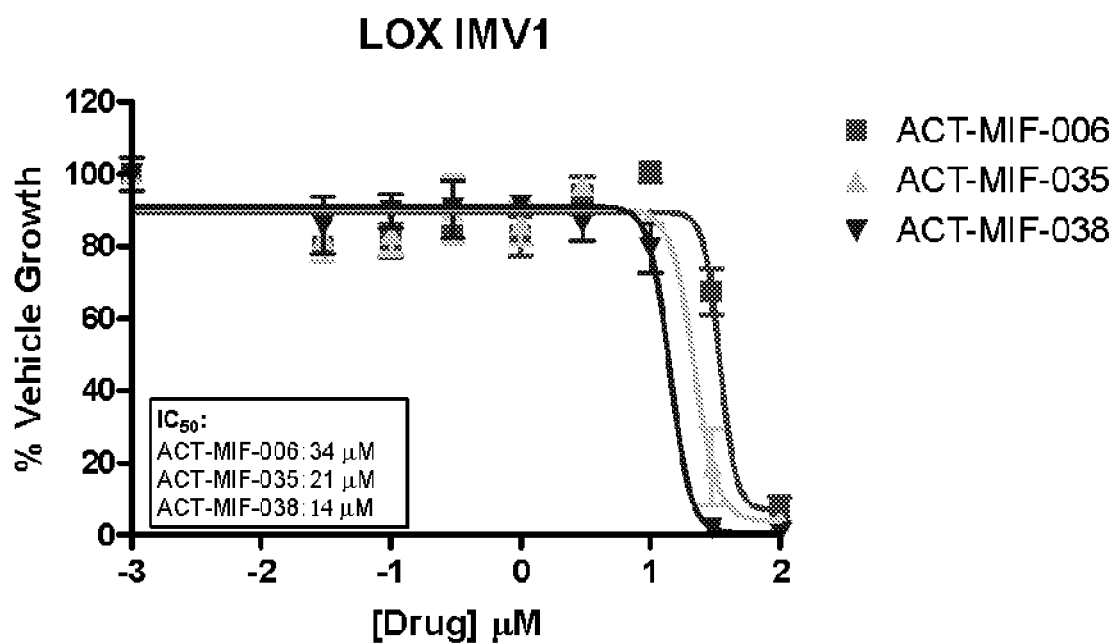
FIG. 6 depicts inhibition of cell proliferation IC50 values for ACT-MIF-006, ACT-MIF-035, and ACT-MIF-038 in the LOX-IMV1 tumor cell line.
Figure 7:
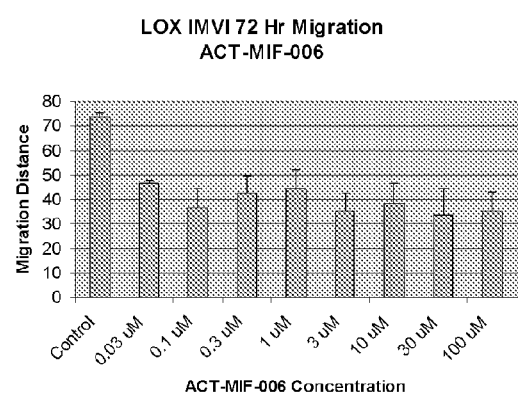
FIG. 7 depicts inhibition of cell migration in the LOX-IMV1 tumor cell line at 72 hrs, for ACT-MIF-006 (A), ACT-0035 (B and D), and ACT-MIF-038. Results indicate a significant inhibition of migration, even at low concentrations (0.03 uM).
Figure 7:
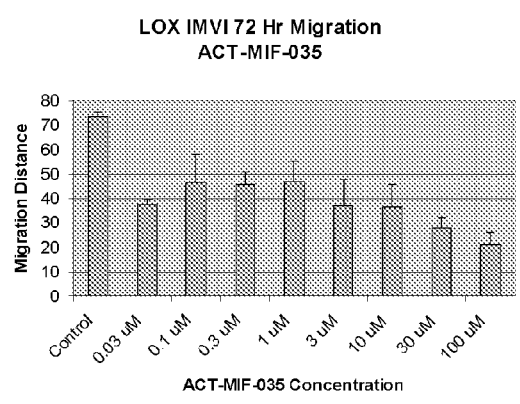
Figure 7:
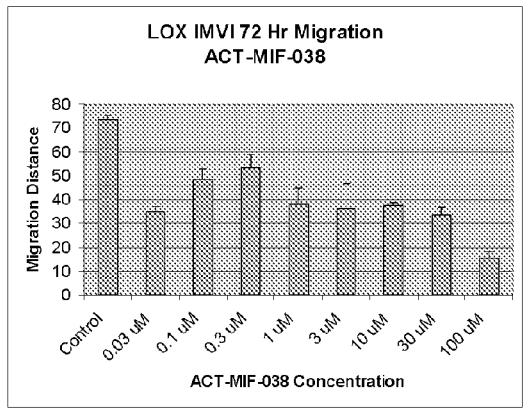
Figure 7:
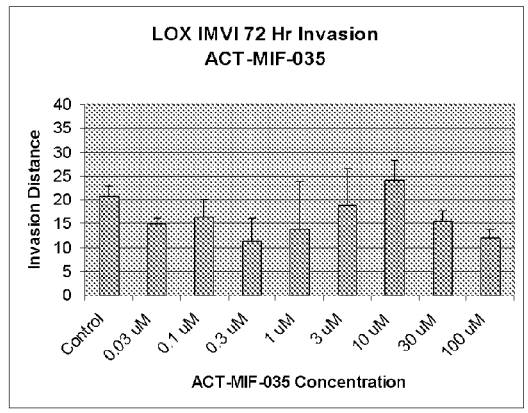

The LOX-IMV1 tumor cell line was used to determine the inhibition of cell migration using the Oris Cell Migration Assay kit (Promega, MI). Briefly, adherent cells were seeded into each well of the kit according to kit instructions. Concentrations of cells in the migration zone were determined to calculate IC50 values. Prior to the migration assay, cell proliferation IC50s were determined to differentiate between inhibition of proliferation and migration. Results are shown in FIGS. 6 and 7. Results show a significant inhibition of migration even at very low concentration (0.03 µM). A slightly modified method was also used to determine the inhibition of invasion. As shown in FIG. 7, invasion was also inhibited.

Example 67

Determination of the Anti-Angiogenic Properties in the Chick Chorioallantoic Membrane (CAM) Assay 8 groups with 10 embryos in each group were used in the experiment described below. Fresh fertile eggs were incubated for 3 days in a standard egg incubator at 37° C. for 3 days. On Day 3, eggs were cracked under sterile conditions and embryos were placed into 20×100 mm plastic plates and cultivated at 37° C. in an embryo incubator with a water reservoir on the bottom shelf. Air was continuously bubbled into the water reservoir using a small pump so that the humidity in the incubator is kept constant. On Day 6, a sterile silicon "o" ring was placed on each CAM and test compound dissolved in 0.5% methylcellulose was placed into each "o" ring in a sterile hood. Paclitaxel was used as a positive control. Embryos were returned to the incubator after addition of test material. Control embryos received 10 µL of vehicle alone. On Day 8, embryos were removed from the incubator and kept at room temperature while blood vessel density were determined under each "o" ring using an image capturing system at a magnification of 160×. The blood vessel density was measured using an angiogenesis scoring system in that arithmetic numbers 0 to 5 (or exponential numbers 1 to 32) are used to indicate number of blood vessels present at the treatment sites on the CAM. Number 5 represents the highest density and 0 represents no angiogenesis. The percent of inhibition at each dosing site was calculated using the score recorded for that site divided by the mean score obtained from the appropriate control samples for each individual experiment. The percent of inhibition for each dose of a given compound was calculated by pooling all results obtained for that dose from 8-10 embryos. Results are summarized in Table 8 below and demonstrate that among others, compounds ACT-MIF-001, ACT-MIF-002, and ACT-MIF-003 have high anti-angiogenic properties.

TABLE 8

Blood vessel densities

| Conc per CAM | | Blood Vessel Density | | | |
|---|---|---|---|---|---|
| | — | 6 nM | 0.3 nM | 3 nM | 30 nM |
| Control | 14.0 ± 3.2 | | | | |
| Paclitaxel | | 2.8 ± 0.7 | | | |
| ACT-MIF-001 | | | 10.5 ± 3.4 | 4.1 ± 0.8 | 1.8 ± 0.3 |
| ACT-MIF-002 | | | 9.4 ± 2.4 | 8.6 ± 2.6 | 4.4 ± 1.3 |
| ACT-MIF-003 | | | 11.6 ± 1.2 | 4.2 ± 1.2 | 4.1 ± 0.7 |

Another experiment was performed using a protocol similar to the one described above but using matrigel plugs instead of o ring to deliver the test material to the CAM. Results are summarized in Table 9 below and show a statistically significant inhibition of angiogenesis at the high concentrations of test material.

TABLE 9

Blood vessel densities

| Conc per CAM | | Blood Vessel Counts | | | |
|---|---|---|---|---|---|
| | — | 2 nM | 0.3 nM | 3 nM | 30 nM |
| Control | 39.3 ± 1.3 | | | | |
| Paclitaxel | | 15.5 ± 2.1 | | | |
| ACT-MIF-006 | | | 38.8 ± 3.5 | 35.8 ± 5.4 | 33.5 ± 1.7 |
| ACT-MIF-030 | | | 35.6 ± 1.0 | 32.7 ± 3.2 | 28.1 ± 2.0 |
| ACT-MIF-035 | | | 28.3 ± 1.7 | 27.3 ± 2.4 | 26.7 ± 1.9 |
| ACT-MIF-038 | | | 31.8 ± 5.8 | 33.6 ± 1.7 | 31.0 ± 4.1 |

Example 68

Pharmacokinetics Parameters

The pharmacokinetic parameters of several compounds were investigated in rodents. Both oral and iv administration were investigated in rats. Blood samples were collected over time; plasma was analyzed using an LC/MS-MS method. Pharmacokinetic parameters were calculated using WinNonLin. Terminal plasma half-lives were 7.10 hr for ACT-MIF-001, 1.66 hr for ACT-MIF-002, and 1.50 hr for ACT-MIF-003. After i.v. administration, the clearance values were 45753 mL/hr/kg for ACT-MIF-001, 7911 mL/hr/kg for ACT-MIF-002, and 11827 mL/hr/kg for ACT-MIF-003. The volume of distribution values were 72666 mL/kg for ACT-MIF-001, 2118 mL/kg for ACT-MIF-002, and 1926 mL/kg for ACT-MIF-003.

Example 69

In Vivo Efficacy in Xenograft Tumor Models

Figure 8:
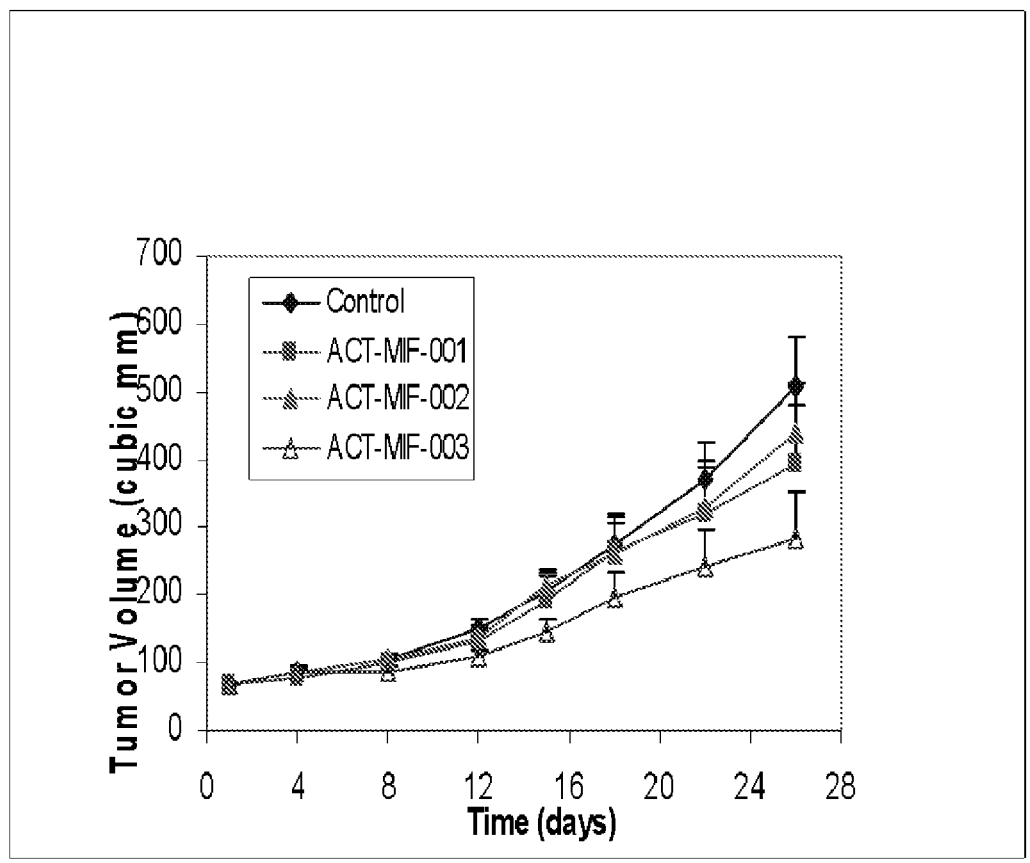
FIG. 8 depicts tumor growth inhibition of DU145 human prostate xenografts in athymic nude mice treated with ACT-MIF-001, ACT-MIF-002, and ACT-MIF-003. Results show ACT-MIF-003 significantly inhibited tumor growth.

Athymic nude mice at 7-8 weeks of age were used for the study. Mice were housed in microisolator housing, with food and water provided as libitum, and quarantined for 4 days prior to the initiation of the study. DU145 cells were maintained in McCoy's 5A medium supplemented with 10% fetal bovine serum and 2 mM glutamine. Cells at 80% confluence were harvested using 0.25% trypsin/EDTA solution, washed once with PBS and resuspended in a mixture of serum-free medium/Matrigel (1:1 by volume) at a density of $3\times10^6$ cells/100 µl groups of 10 mice each were used in the experiment. DU145 cells suspended in 100 µl of a mixture of medium/Matrigel (1:1) were subcutaneously implanted in the right flank region. Animals were monitored for tumor growth daily after cell implantation. When tumor volumes reached 80-100 mm³, mice were randomized into 4 groups of 10 mice each using only mice having tumor volumes closest to the mean value. Tumor volumes were measured using the formula $V = L \times W \times H \times \pi/6$, where L and W represent the longer and shorter diameters of the tumor and H represents the height of the tumor. Treatment began the day after randomization. Act-MIF-001, ACT-MIF-002, and ACT-MIF-003 were administered daily by IP injection at a dose of 40 mg/kg for 4 weeks. Throughout the entire study, tumor volumes were measured twice weekly and body weights once weekly. Animals were observed for possible toxic effect from the drug treatment. Results illustrated below in FIG. 8 demonstrated that ACT-MIF-003 significantly inhibited tumor growth.

Example 70

Determination of the Microvessel Density in Xenograft Tumors

Figure 9:
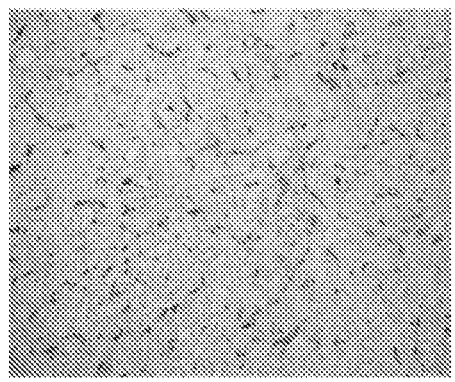
FIG. 9 depicts tumor slices from animals treated with control (A), ACT-MIF-002 (B), ACT-MIF-001 (C), and ACT-MIF-003 (D). Blood vessel density of the tumor tissues was measured by immunohistochemistry. Results indicated a decrease in microvessel density with respect to the tumors of the control group with a statistically meaningful difference for the ACT-MIF-003 treated group.
Figure 9:
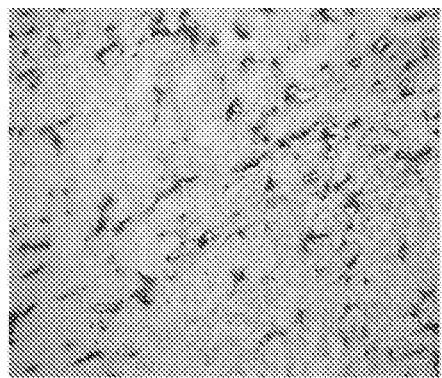
Figure 9:
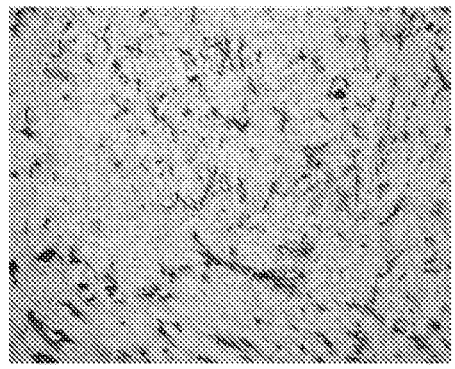
Figure 9:
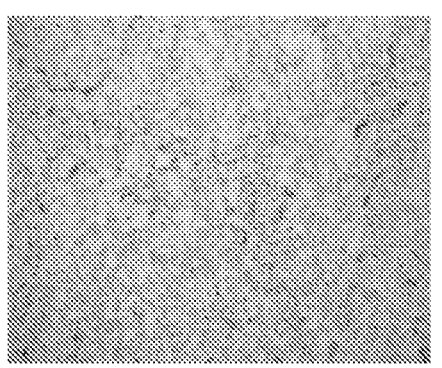

At the end of the experiment described in example 69 above, tumors in each group were removed and sliced. Blood vessel density of the tumor tissues was measured by immunohistochemistry. Results indicated a decrease in microvessel density with respect to the tumors of the control group with a statistically meaningful difference for the ACT-MIF-003 treated group. These in vivo results confirmed that the compounds described in this application inhibit angiogenesis. Representative pictures of the stained tissues are showed in FIG. 9.

Example 71

Efficacy Study in a Pancreatic Tumor Model

Figure 10:
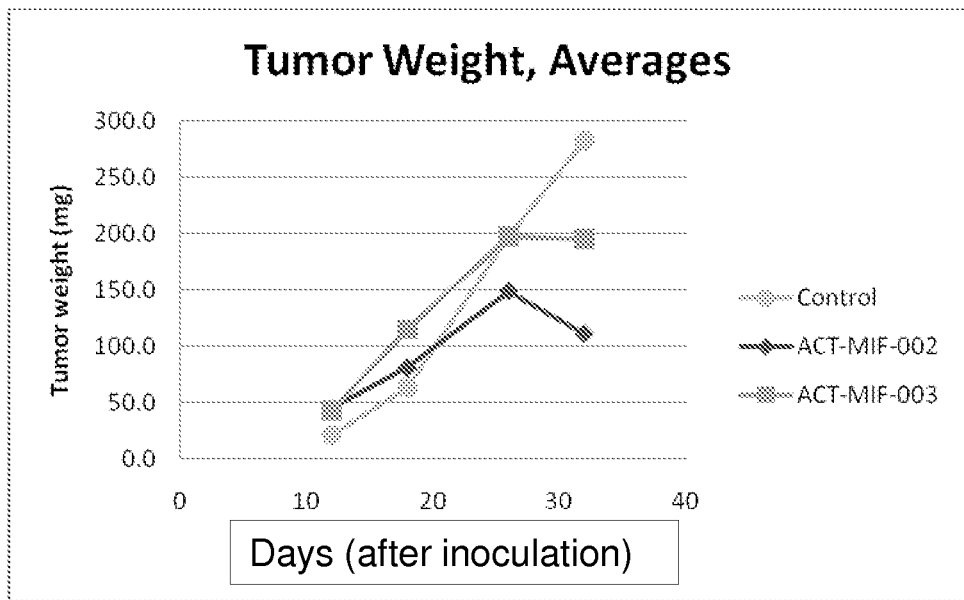
FIG. 10 depicts tumor growth inhibition (A) and survival data (B) in a pancreatic tumor model treated with control, ACT-MIF-002, and ACT-MIF-003. Results indicate the tested compounds had significant impact on survival and limited metastatic tumor burden.
Figure 10:
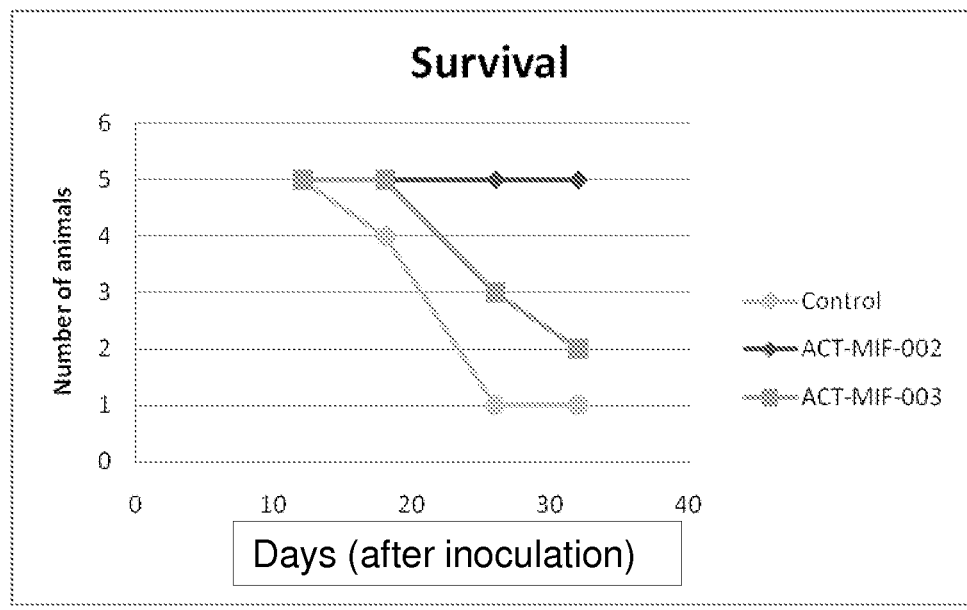

The activity of the compounds of the invention was investigated in a pancreatic tumor model using an experiment similar to the one described in Example 69. Compounds ACT-MIF-002 and ACT-MIF-003 were dosed daily at 40 mg/kg via IP administration. Results shown in FIG. 10 indicated that the compounds of the invention tested in this experiment had a significant impact on survival and that limited the metastatic tumor burden as shown in the survival graph and representative histopathologic slides (FIG. 11) of the lumbar region of control and treated animals. In addition, animal weights were monitored throughout the study; there was no body weight loss and no clinical signs of toxicity indicating that these compounds are very well tolerated.

Figure 11:
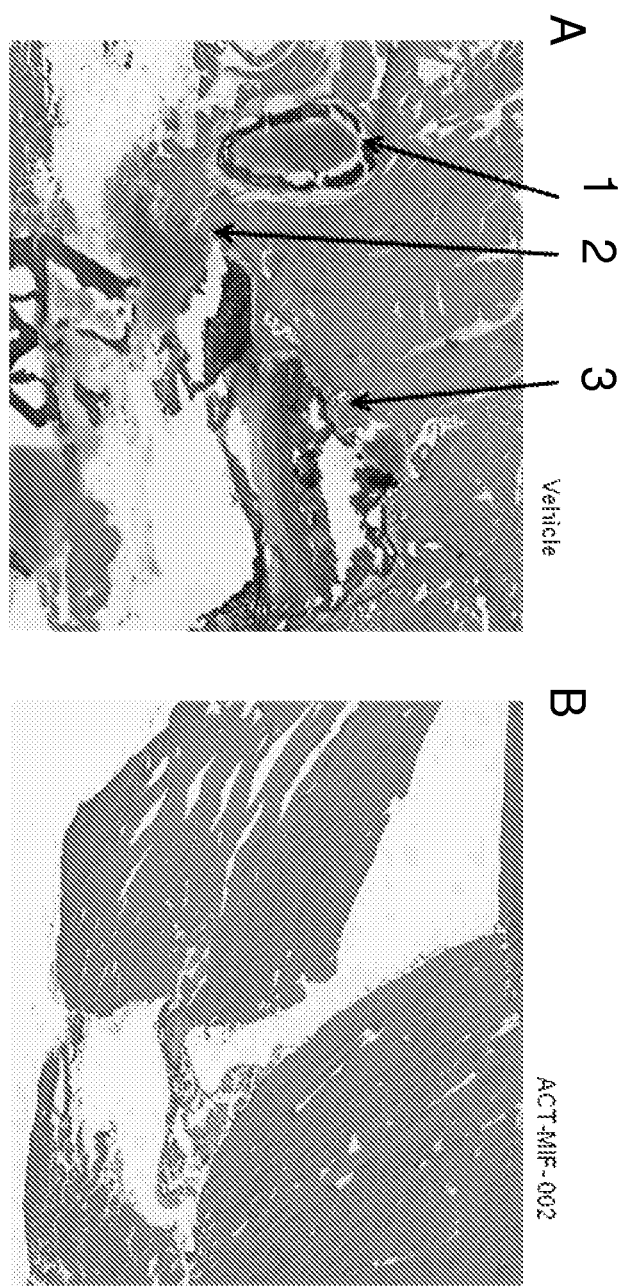
FIG. 11 depicts histopathological slides comparing bone marrow from pancreatic tumor model animals treated with control (A) and ACT-MIF-002. Bone marrow of the vehicle treated mice is consistent with bone metastases (1) with evidence of surrounding skeletal muscle metastases from invading marrow tumor cells (2 and 3). No evidence of bone metastases was observed with spinal column sections from ACT-MIF-002 treated mice.

Lumbar regions of the control and treated groups were excised and sent for histopathological evaluation. As shown in FIG. 11, there were significant differences between control and treated groups as there was no evidence of bone metastases in the ACT-MIF-002 treated group. In the example shown in FIG. 11, bone marrow of the vehicle treated mice is consistent with bone metastases (1) with evidence of surrounding skeletal muscle metastases from invading marrow tumor cells (2 and 3). No evidence of bone metastases was observed with spinal column sections from ACT-MIF-002 treated mice.

Example 72

Oral Bioavailability

Figure 12:
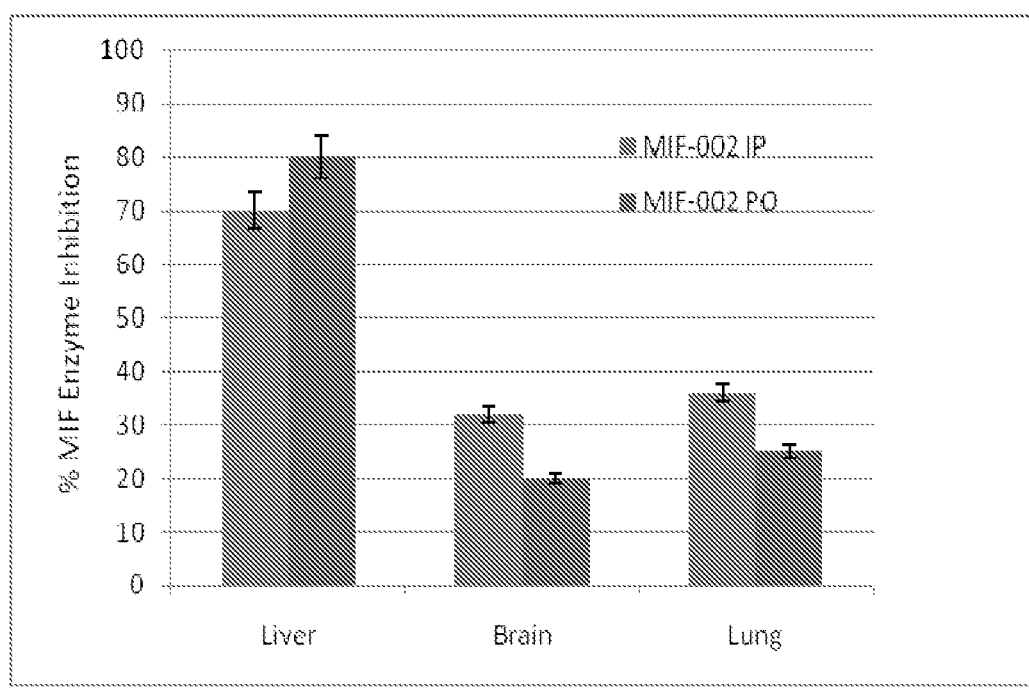
FIG. 12 depicts a comparison of MIF enzyme inhibition in the liver, brain, and lung of healthy animals administered ACT-MIF-002 either intraperitoneally (IP) or per oral (PO). Results indicate the compound is orally bioavailable, crosses the brain blood barrier, and inhibits MIF enzymatic activity in both the brain and the lungs.

The compounds were administered orally (PO) and intraperitoneally (IP) to healthy animals. The inhibition of the MIF liver enzymatic activity determined ex vivo following IP and PO dosing is similar, indicating high oral bioavailability. Furthermore, brain and lung tissues were collected and processed to determine MIF enzymatic activity in these organs. Results also shown in FIG. 12 are indicative of an excellent tissue distribution and demonstrate significant MIF inhibition in both the brain and lungs. As shown in FIG. 12, MIF-002, is orally bioavailable. Inhibition of MIF enzyme was determined in vitro following dosing of MIF-002 at 40 mg/kg once a day for three days, both IP and PO (normal C57BL6 mice, n=3). Tissues were collected at sacrifice and processed. Liver, lung, and brain tissues were collected, processed, and used for the determination of MIF enzyme activity. Values are expressed as a percentage calculated using DMSO as control (no inhibition).

Two additional compounds were tested, MIF-035 and MIF-041. Results (data not shown) indicated that these compounds were also orally bioavailable, crossed the blood brain barrier, and inhibited MIF enzymatic activity very efficiently in all three organs with results varying ~12% inhibition in liver extracts to ~76.2% inhibition in the lungs.

Results indicate compounds of the invention are orally bioavailable, cross the brain blood barrier, and inhibit MIF enzymatic activity in both the brain and the lungs.

Example 73

4-IPP and ACT-003 Inhibit T Lymphocyte Activation

Figure 13:
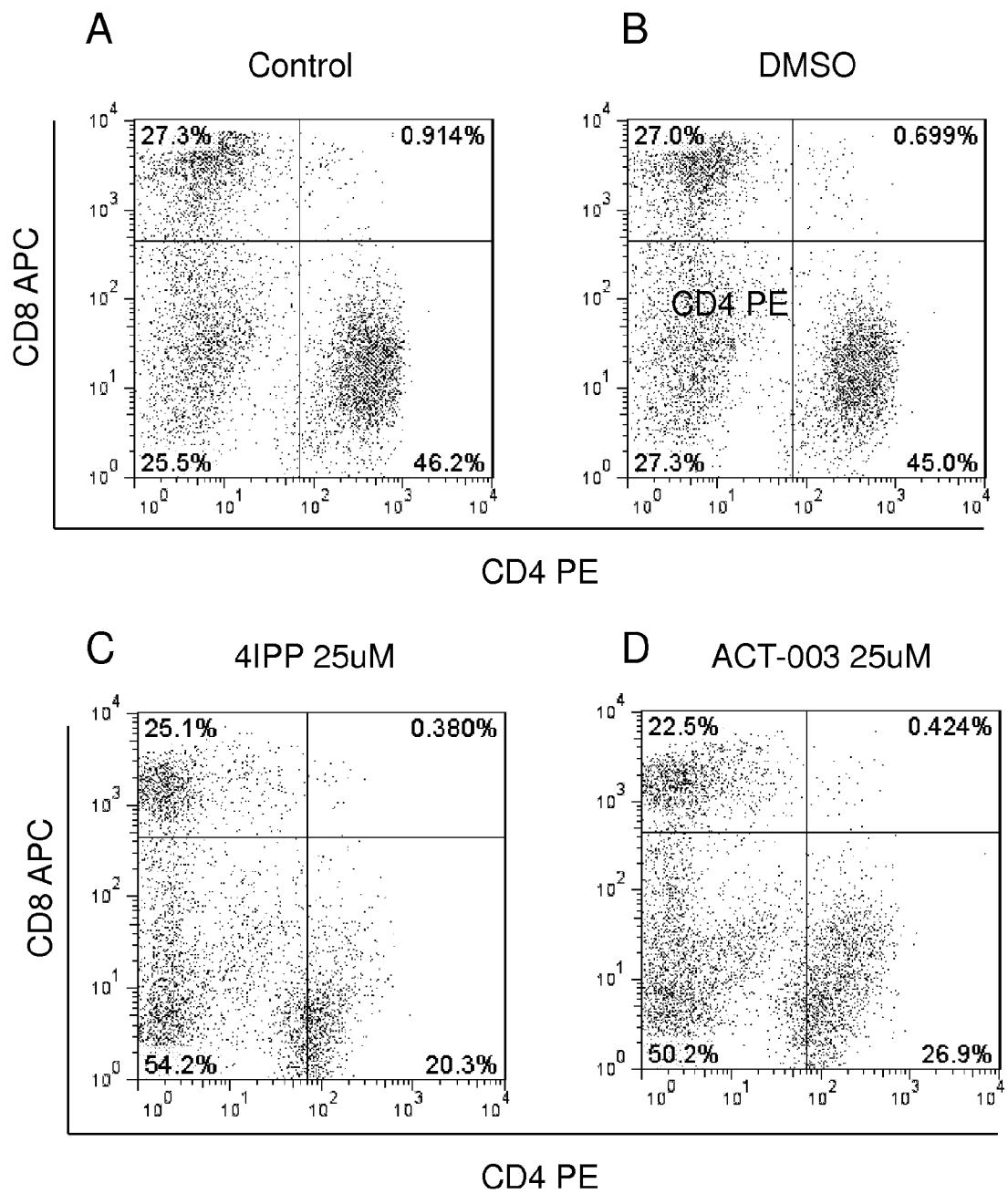
FIG. 13 depicts 4-IPP-based MIF antagonists effects on primary T lymphocyte activation/proliferation. Fresh, primary human T lymphocytes was collected by aphaeresis and separated by Ficoll gradents. $1 \times 10^6$ lymphocytes were added to immobilized anti-CD3 tissue culture plates in the presence of nothing (control), vehicle control (0.1% DMSO, 25 µM 4-IPP or 25 µM ACT-003. 48 hours later cells were collected, washed and stained with anti-CD4 and ant-CD8 labeled antibodies followed by flow cytometric analyses. Shown are the relative percentages of CD4/CD8 lymphocytes.
Figure 14:
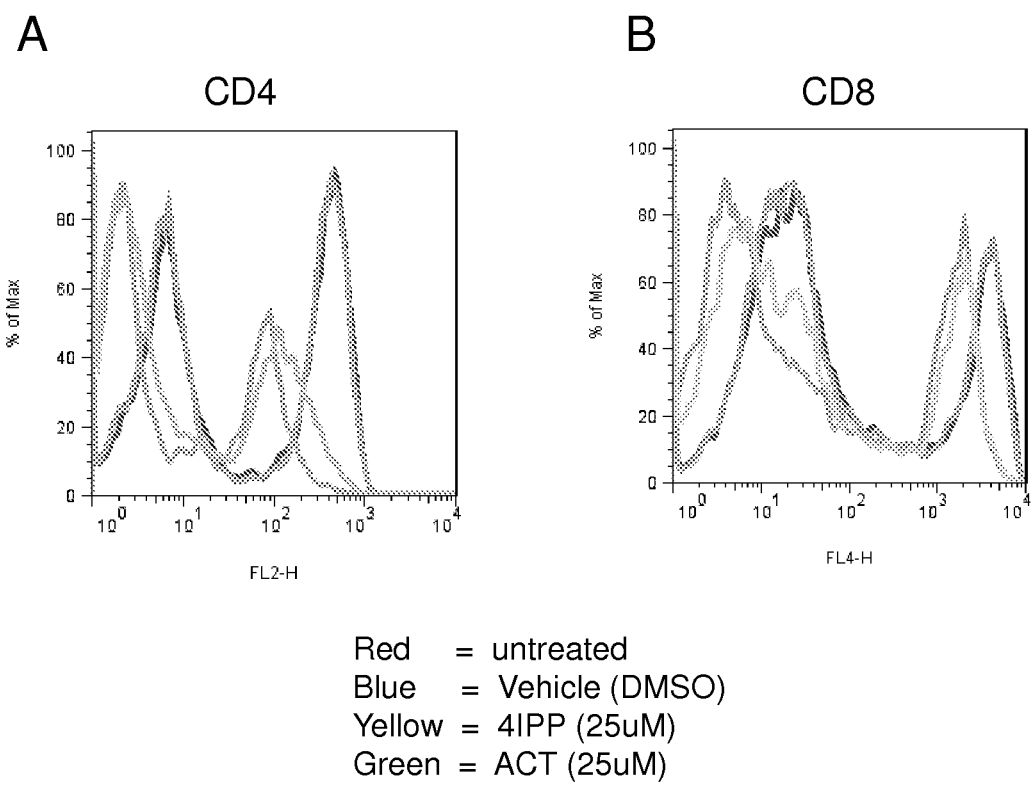
FIG. 14 depicts the data from FIG. 15 as an overlay of relative fluorescence intensity.

In order to assess the ability of MIF antagonists to disrupt autoimmune-associated T cell activation, primary human T lymphocytes were prepared using standard Ficoll-gradient preparations. $1 \times 10^6$ lymphocytes/ml were resuspended in RPMI/10% FCS and plated onto anti-CD3 antibodies previously immobilized onto tissue culture plates. Control, vehicle control (0.1% DMSO), 25 µM 4-IPP or 25 µM ACT-003 were added to cells and allowed to incubate for 48 hours. Cells were lifted, washed and stained with anti-CD4 or anti-CD8 antibodies and then analyzed by flow cytometry. As shown in FIGS. 13 and 14, cells treated with MIF antagonists 4-IPP and ACT-003 during anti-CD3 lymphocyte activation had significantly fewer CD4 and CD8 T lymphocytes suggesting defective anti-CD3 induced activation/proliferation in MIF inhibitor treated lymphocytes.

Figure 15:
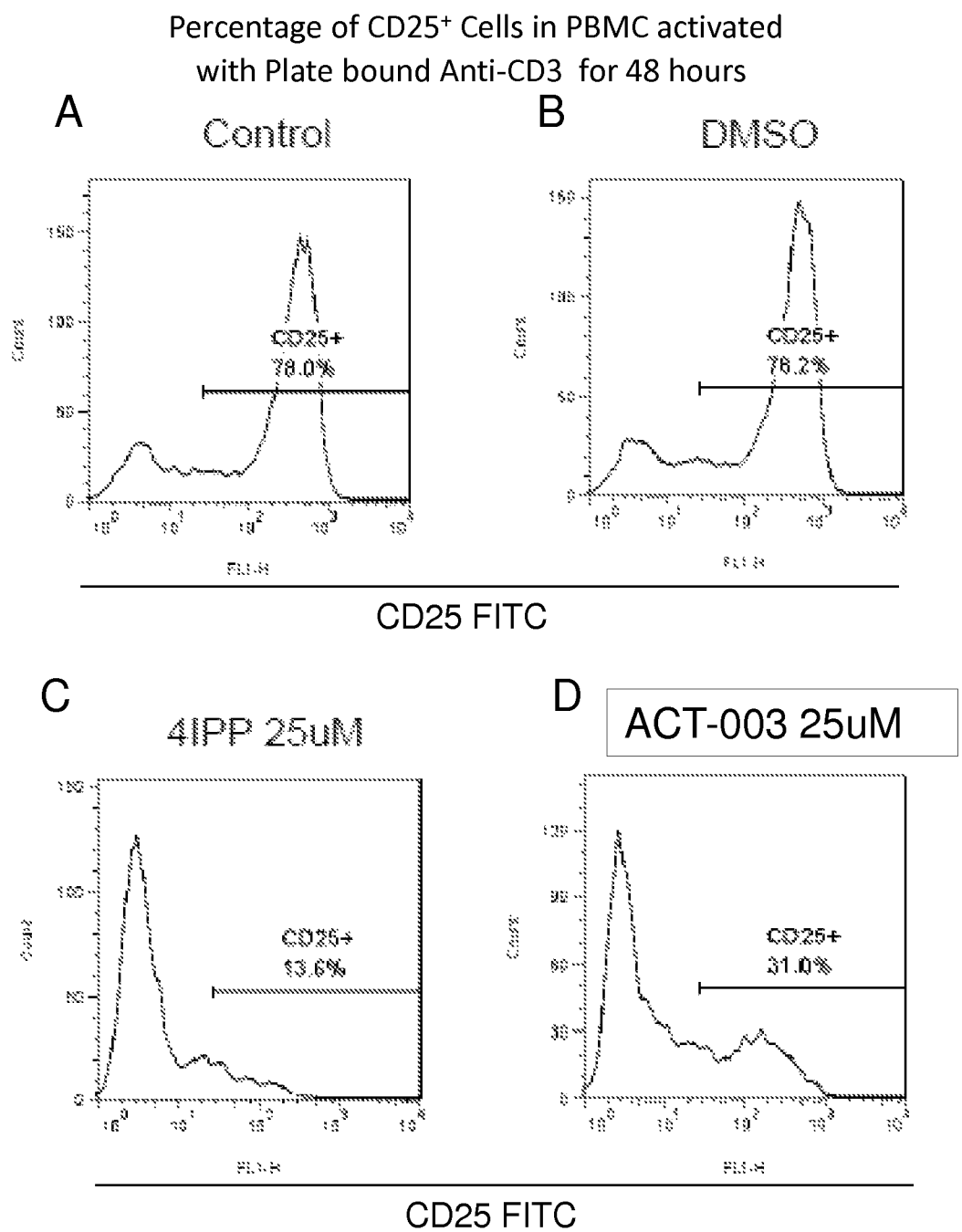
FIG. 15 depicts 4-IPP-based MIF antagonists effects on primary T lymphocyte activation/proliferation. Fresh, primary human T lymphocytes was collected by aphaeresis and separated by Ficoll gradents. $1 \times 10^6$ lymphocytes were added to immobilized anti-CD3 tissue culture plates in the presence of nothing (control), vehicle control (0.1% DMSO, 25 µM 4-IPP or 25 µM ACT-003. 48 hours later cells were collected, washed and stained with an anti-CD25-labeled antibody followed by flow cytometric analyses. CD25 (high affinity IL-2 receptor) is a commonly used marker for T lymphocyte activation. Shown are the relative percentages of CD25+(i.e. activated) treated vs. untreated lymphocytes.
Figure 16:
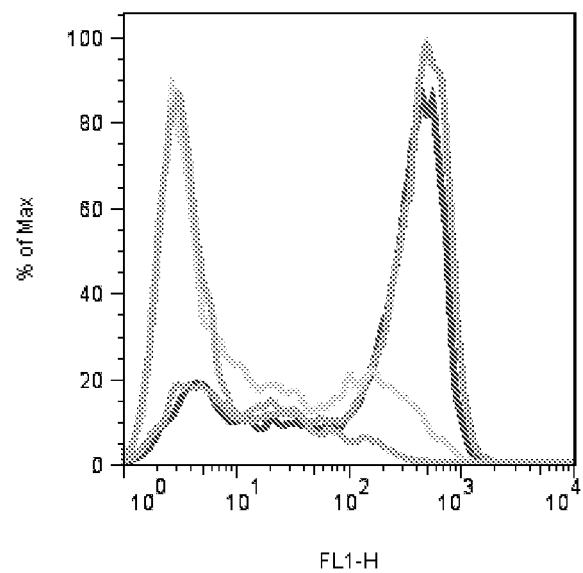
FIG. 16 depicts the data from FIG. 17 as an overlay of fluorescence intensity.

To validate the effects of MIF antagonists on T lymphocyte activation, experiments were set up exactly as described above and, 48 hours later, treated and untreated lymphocytes were stained with an anti-CD25 antibody. CD25 is also known as the high affinity IL-2 receptor—a very well characterized and frequently marker of T lymphocyte activation. As shown in FIGS. 15 and 16, 4-IPP and ACT-003 almost completely blocked the anti-CD3-induced CD25 expression suggesting a nearly complete block of T lymphocyte activation.

Figure 17:
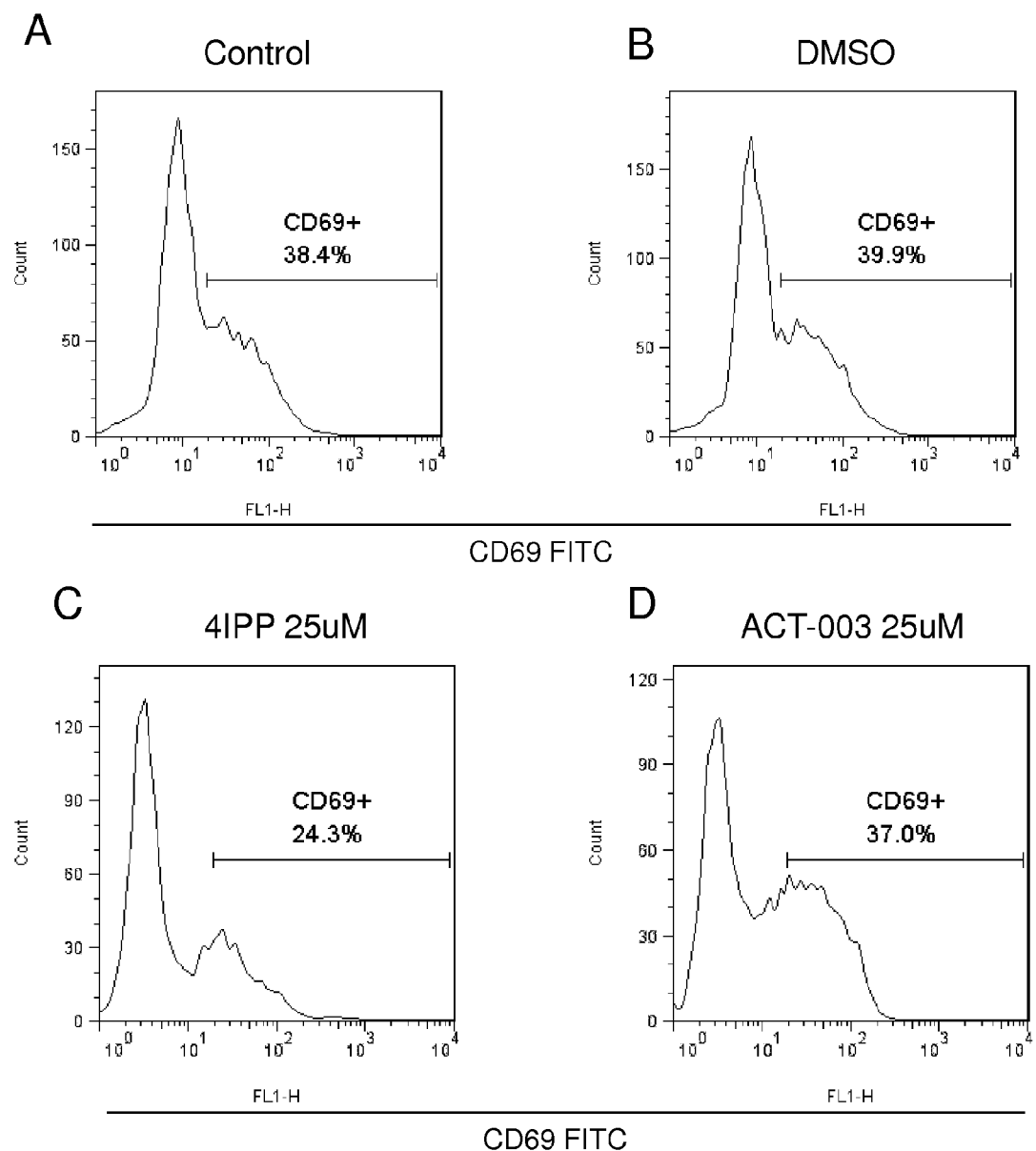
FIG. 17 depicts 4-IPP-based MIF antagonists effects on primary T lymphocyte activation/proliferation. Fresh, primary human T lymphocytes was collected by aphaeresis and separated by Ficoll gradients. $1 \times 10^6$ lymphocytes were added to immobilized anti-CD3 tissue culture plates in the presence of nothing (control), vehicle control (0.1% DMSO, 25 µM 4-IPP or 25 µM ACT-003. 16 hours later cells were collected, washed and stained with an anti-CD69-labeled antibody followed by flow cytometry analysis. CD69 is an early marker of lymphocyte activation and the lack of a large effect on early lymphocyte activation suggests that treatment of established T cell-dependent autoimmune diseases with 4-IPP-based anti-MIF antagonists is feasible. Shown are the relative percentages of CD69 on treated vs. untreated lymphocytes.
Figure 18:
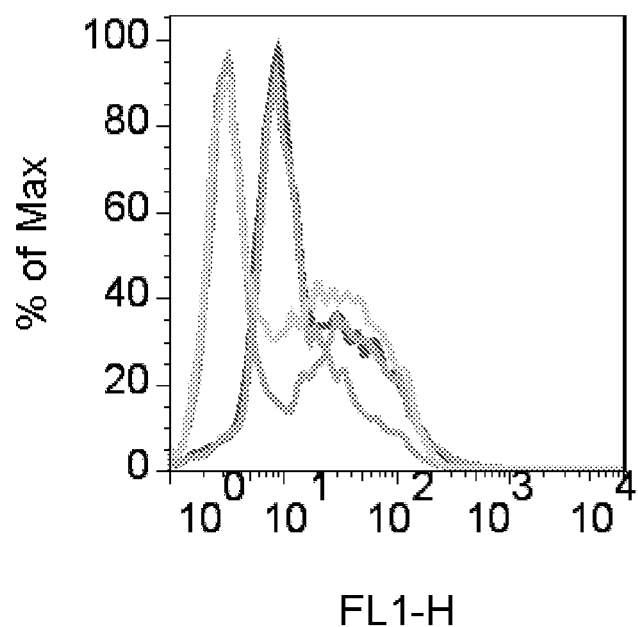
FIG. 18 depicts the data from FIG. 19 as an overlay of fluorescence intensity.

In order to investigate the relative kinetics of when 4-IPP and ACT-003 are acting in blocking T lymphocyte activation, we repeated the experiment described above but harvested lymphocytes only 16 hours after anti-CD3 plating. At this early time point during T lymphocyte activation, CD69 is found to be expressed and is usually considered to be an "early marker" of lymphocyte activation. As shown in FIGS. 17 and 18, treatment with MIF antagonists had only a marginal effect on CD69 expression suggesting that MIF inhibitors are acting at a relatively late stage in the activation process. This is important because it suggests that therapeutic use of 4-IPP-based MIF inhibitors in autoimmune diseases can be used at later stages and aren't likely to be required to be delivered in the early stages of disease onset.

Figure 19:
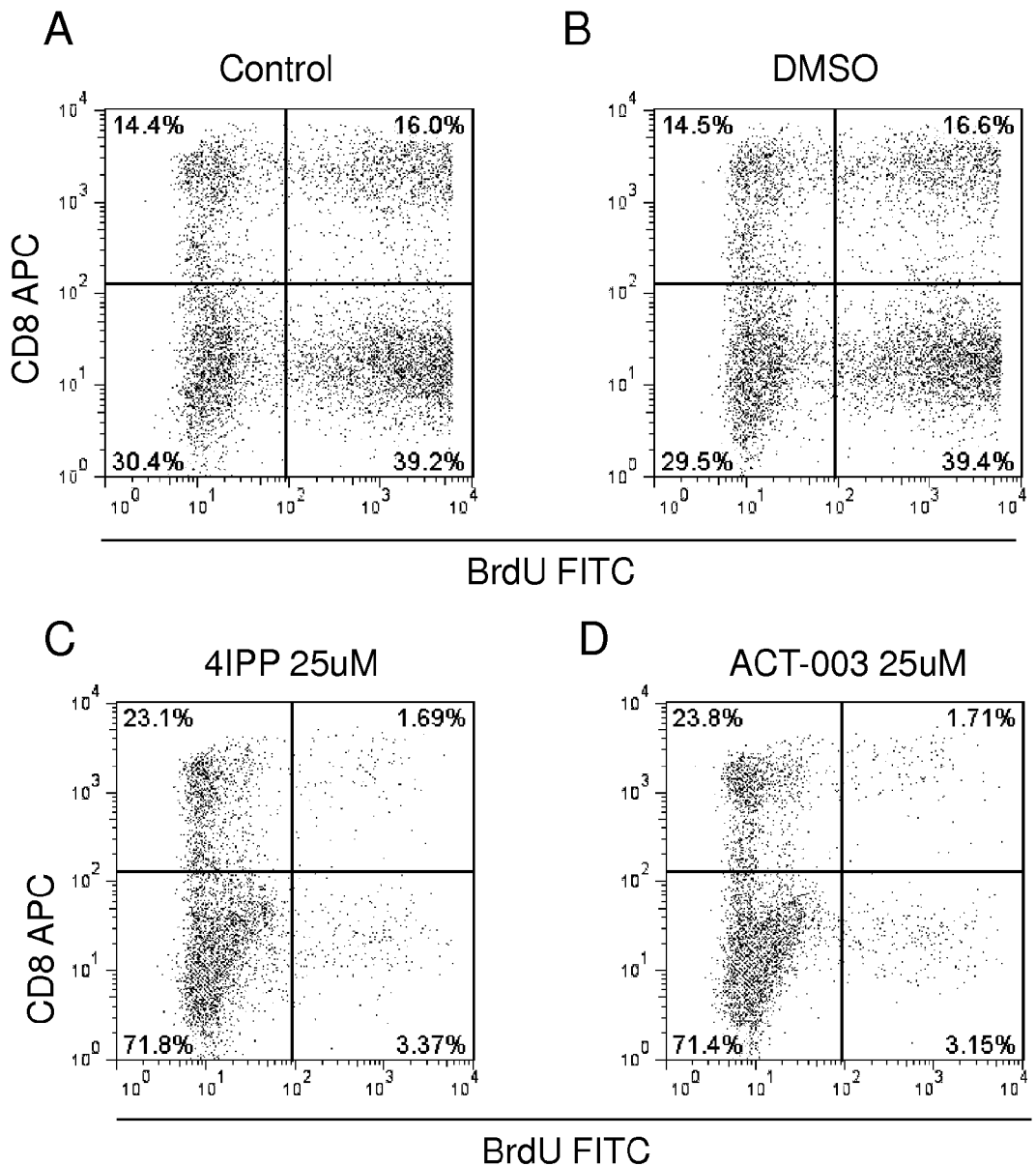
FIG. 19 depicts 4-IPP-based MIF antagonists' effects on primary T lymphocyte activation/proliferation. Fresh, primary human T lymphocytes was collected by aphaeresis and separated by Ficoll gradients. $1 \times 10^6$ lymphocytes were added to immobilized anti-CD3 tissue culture plates in the presence of nothing (control), vehicle control (0.1% DMSO, 25 µM 4-IPP or 25 µM ACT-003. 48 hours later labeled-BrdU was added to the cells briefly, then washed, stained with labeled-anti-CD8 antibodies and analyzed for BrdU incorporation into DNA (readout for proliferation) by flow cytometry.
Figure 20:
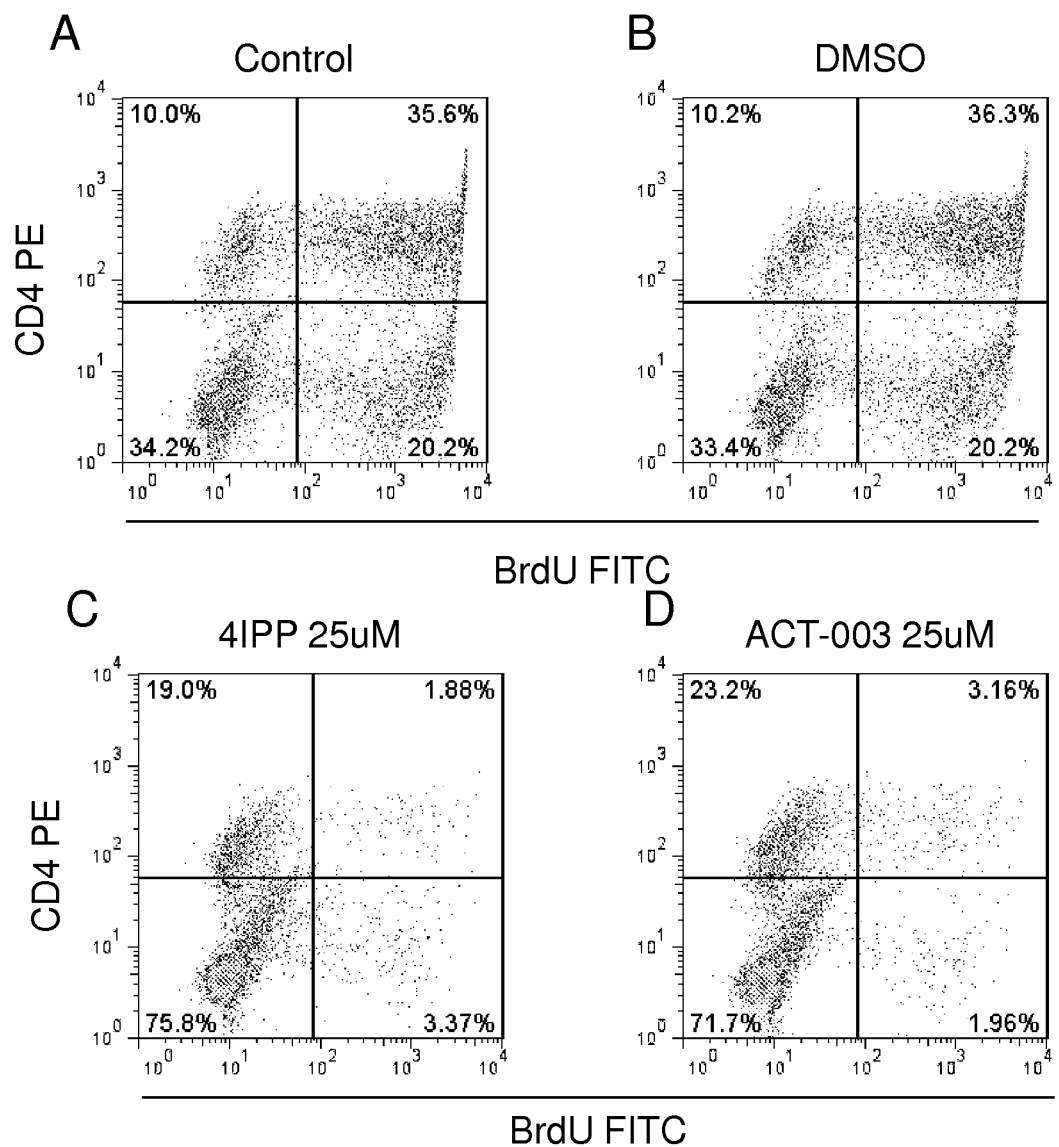
FIG. 20 depicts 4-IPP-based MIF antagonists' effects on primary T lymphocyte activation/proliferation. Fresh, primary human T lymphocytes was collected by aphaeresis and separated by Ficoll gradients. $1 \times 10^6$ lymphocytes were added to immobilized anti-CD3 tissue culture plates in the presence of nothing (control), vehicle control (0.1% DMSO, 25 µM 4-IPP or 25 µM ACT-003. 48 hours later labeled-BrdU was added to the cells briefly, then washed, stained with labeled-anti-CD4 antibodies and analyzed for BrdU incorporation into DNA (readout for proliferation) by flow cytometry.

Finally, to confirm that proliferation of CD4+ and CD8+T lymphocytes is blocked by 4-IPP-based MIF antagonists, we repeated the experiment as described above, added labeled-BrdU to cells, stained with either labeled anti-CD4 or anti-CD8 antibodies and then assessed relative CD4/CD8 and BrdU labeling in each treatment group. As shown in FIGS. 19 and 20, 4-IPP and ACT-003 almost completely blocked BrdU labeling in both CD8+ and CD4+T lymphocytes.

Combined, these results suggest that targeting MIF using these 4-IPP-based small molecules may have profound inhibitory effects on T lymphocyte-dependent autoimmune disorders.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A migration inhibitory factor (MIF) inhibitory compound, or its enantiomeric or diastereomeric form or a pharmaceutically acceptable salt, prodrug, or metabolite thereof, said MIF inhibitory compound having the formula:

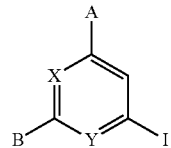

Formula I wherein:
A is a substituted or unsubstituted bicyclic ring selected from the group consisting of quinoline, isoquinoline, benzofuran, and benzothiophene;
B is H;
X and Y are both N,
and further wherein the MIF inhibitory compound interacts with a MIF polypeptide to inhibit an enzymatic activity of the MIF polypeptide.

2. The compound of claim 1, wherein the compound is selected from the group consisting of:
4-Iodo-6-(isoquinolin-4-yl)pyrimidine;
4-Iodo-6-(quinolin-4-yl)pyrimidine;
4-Iodo-6-(quinolin-8-yl)pyrimidine;
4-Iodo-6-(quinolin-3-yl)pyrimidine;
4-Iodo-6-(isoquinolin-5-yl)pyrimidine;
4-Iodo-6-(benzothiophen-2-yl)pyrimidine; and
4-Iodo-6-(benzofuran-2-yl)pyrimidine.

3. A pharmaceutical composition comprising:
a) a safe and effective amount of a MIF inhibitory compound of claim 1; and
b) one or more pharmaceutically acceptable excipients.

4. The pharmaceutical composition of claim 3, wherein the compound is selected from the group consisting of 4-Iodo-6-(isoquinolin-4-yl)pyrimidine; 4-Iodo-6-(quinolin-4-yl)pyrimidine; 4-Iodo-6-(quinolin-8-yl)pyrimidine; 4-Iodo-6-(quinolin-3-yl)pyrimidine; 4-Iodo-6-(isoquinolin-5-yl)pyrimidine; 4-Iodo-6-(benzothiophen-2-yl)pyrimidine; and 4-Iodo-6-(benzofuran-2-yl)pyrimidine.

5. A compound selected from the group consisting of 4-Iodo-6-(isoquinolin-4-yl)pyrimidine; 4-Iodo-6-(quinolin-4-yl)pyrimidine; 4-Iodo-6-(quinolin-8-yl)pyrimidine; 4-Iodo-6-(quinolin-3-yl)pyrimidine; 4-Iodo-6-(isoquinolin-5-yl)pyrimidine; 4-Iodo-6-(benzothiophen-2-yl)pyrimidine; and 4-Iodo-6-(benzofuran-2-yl)pyrimidine.

* * * * *